(12) United States Patent
Hsu et al.

(10) Patent No.: US 9,275,009 B2
(45) Date of Patent: Mar. 1, 2016

(54) CALIBRATION AND CONSISTENCY CHECK OF VARIABLE VOLUME SYSTEMS

(75) Inventors: Kai Hsu, Sugar Land, TX (US); Kentaro Indo, Sugar Land, TX (US); Sihar Marpaung, Issy les Moulineaux (FR); Peter S. Hegeman, Stafford, TX (US); Michael Toribio, Toronto (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 647 days.

(21) Appl. No.: 13/596,996

(22) Filed: Aug. 28, 2012

(65) Prior Publication Data
US 2013/0110401 A1 May 2, 2013

Related U.S. Application Data

(60) Provisional application No. 61/530,617, filed on Sep. 2, 2011.

(51) Int. Cl.
| G06F 17/00 | (2006.01) |
| G01V 13/00 | (2006.01) |
| G01N 33/28 | (2006.01) |
| G01N 7/16  | (2006.01) |

(52) U.S. Cl.
CPC .......... *G06F 17/00* (2013.01); *G01N 33/2823* (2013.01); *G01V 13/00* (2013.01); *G01N 7/16* (2013.01)

(58) Field of Classification Search
CPC ................................................. G01N 33/2823
See application file for complete search history.

(56) References Cited

U.S. PATENT DOCUMENTS

| 3,702,564 A | 11/1972 | Chenevert |
| 6,223,588 B1 | 5/2001 | Burgass et al. |
| 6,334,489 B1 | 1/2002 | Shwe et al. |
| 6,412,354 B1 | 7/2002 | Birchak et al. |
| 6,543,281 B2 | 4/2003 | Pelletier et al. |
| 6,688,176 B2 | 2/2004 | Storm, Jr. et al. |
| 7,114,562 B2 | 10/2006 | Fisseler et al. |
| 7,194,902 B1 | 3/2007 | Goodwin et al. |

(Continued)

FOREIGN PATENT DOCUMENTS

| GB | 2304906 | * | 3/1997 |
| GB | 2304906 A | | 3/1997 |

(Continued)

OTHER PUBLICATIONS

Lee, J., Michaels, J. and DiFoggio, R., "Using PV Tests for Bubble Point Pressures and Quality Control", Paper HH, SPWLA 44th Annual Logging Symposium, Jun. 2003: pp. 1-7.

(Continued)

*Primary Examiner* — Phuong Huynh
(74) *Attorney, Agent, or Firm* — Kenneth L. Kincaid

(57) ABSTRACT

Variable volume systems and methods of use thereof described herein are capable of making calibrated determinations of fluid properties and phase behavior of a fluid sample. The determinations can be calibrated based on one or more calibration functions, such as system volume corrected for pressure and temperature variations. Cross-checking the results of measurements can be used to determine accuracy of the calibration or monitor for leaks or other anomalies of the variable volume systems. The variable volume systems can be implemented in a well logging tool and are capable of being calibrated downhole.

18 Claims, 20 Drawing Sheets

(56) References Cited

U.S. PATENT DOCUMENTS

| | | |
|---|---|---|
| 7,222,671 B2 | 5/2007 | Caudwell et al. |
| 7,346,460 B2 | 3/2008 | DiFoggio et al. |
| 7,458,252 B2 | 12/2008 | Freemark et al. |
| 7,461,547 B2 | 12/2008 | Terabayashi et al. |
| 7,574,898 B2 | 8/2009 | Harrison et al. |
| 7,874,199 B2 | 1/2011 | Chaudoreille et al. |
| 7,913,556 B2 | 3/2011 | Hsu et al. |
| 8,335,650 B2 | 12/2012 | Hsu et al. |
| 8,434,356 B2 | 5/2013 | Hsu et al. |
| 8,528,396 B2 | 9/2013 | Wu et al. |
| 2007/0039730 A1* | 2/2007 | Fisseler et al. ............. 166/254.2 |
| 2011/0042070 A1 | 2/2011 | Hsu |

FOREIGN PATENT DOCUMENTS

| | | | |
|---|---|---|---|
| GB | 2377952 | A | 1/2003 |
| GB | 2390677 | A | 1/2004 |
| GB | 2453051 | A | 3/2009 |
| JP | 1019830 | * | 1/1998 |
| JP | 10019830 | A | 1/1998 |
| RU | 2266523 | * | 12/2005 |
| RU | 2266523 | C1 | 12/2005 |
| RU | 2323430 | * | 4/2008 |
| RU | 2323430 | C1 | 4/2008 |
| RU | 2406996 | * | 12/2010 |
| RU | 2406996 | C1 | 12/2010 |
| SU | 396589 | * | 1/1974 |
| SU | 396589 | A1 | 1/1974 |
| SU | 1795726 | A1 | 2/1996 |
| WO | 9208121 | | 5/1992 |
| WO | 2009009409 | A1 | 1/2009 |

OTHER PUBLICATIONS

Retsina, et al., "The theory of a vibrating-rod densimeter", Applied Scientific Research, vol. 43, 1986, pp. 127-158.

International Search Report and Written Opinion for PCT Application No. PCT/US2012/052842 dated Dec. 6, 2012; 8 pages.

* cited by examiner

CALIBRATION AND CONSISTENCY CHECK OF VARIABLE VOLUME SYSTEMS

CROSS-REFERENCE TO RELATED APPLICATIONS

The present application seeks priority to U.S. Provisional Application 61/530,617 filed Sep. 2, 2011, the entirety of which is incorporated by reference.

FIELD OF THE INVENTION

Aspects relate to performing calibration checks for variable volume systems.

BACKGROUND INFORMATION

Accurate measurement of fluid properties and phase behavior of fluids is essential in a variety of fields, for example, in the oil and gas industries.

Traditionally, measurements can be performed in laboratory using a PVT (pressure, volume, and temperature) measurement cell. In addition, various downhole tools can be used for making measurements of pressure-volume (PV) data to derive fluid properties and phase behavior. Such tools provide the opportunity to record data downhole in reservoir conditions. A variety of sensors have been developed for use with various downhole tools, however, the accuracy of fluid properties and phase behavior as determined by these tools and sensors is frequently poor compared to laboratory testing.

Further, results of sensors in downhole tools are sometimes relied upon to take decisions on the foregoing operations. It is therefore desirable to cross-check the results of sensors in downhole tools before relying on the obtained the results, or the PV data of fluid samples.

Accordingly, there is a need in the art for improved systems and methods for calibrating tools used to obtain measurements, and for cross-checking the accuracy or measurements of fluid properties and phase behavior of fluids, that are capable of being performed in a well drilled in the Earth during well logging.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed herein, in one aspect thereof, comprises a method. The method includes the acts of filling a variable volume container of a system with a reference fluid and increasing at least one of the temperature or the pressure of the reference fluid. Additionally, the method includes the act of decreasing at least one of the temperature or pressure of the reference fluid. One or more sensors can record measurements while the at least one of the temperature or the pressure of the reference fluid is decreasing. Further, the method includes the acts of comparing the recorded measurements to one or more known properties of the reference fluid, and calibrating one or more parameters of the system based at least in part on the comparison.

In another aspect, the subject innovation can comprise a system capable of calibrating values of parameters of the system. The system can include a variable volume container that alters at least one of a temperature or a pressure of a reference fluid and a measurement component that records a first set of measurements of the reference fluid while the at least one of the temperature or the pressure of the reference fluid is altered. The system can further include an analysis component that determines a first answer product based at least in part on the first set of measurements and one or more system parameters, wherein the one or more system parameters are uncalibrated. The system can further include a calibration component that determines a calibration function based at least in part on a comparison between the first answer product and one or more known properties of the reference fluid, wherein the calibration component calibrates the one or more system parameters based at least in part on the comparison.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
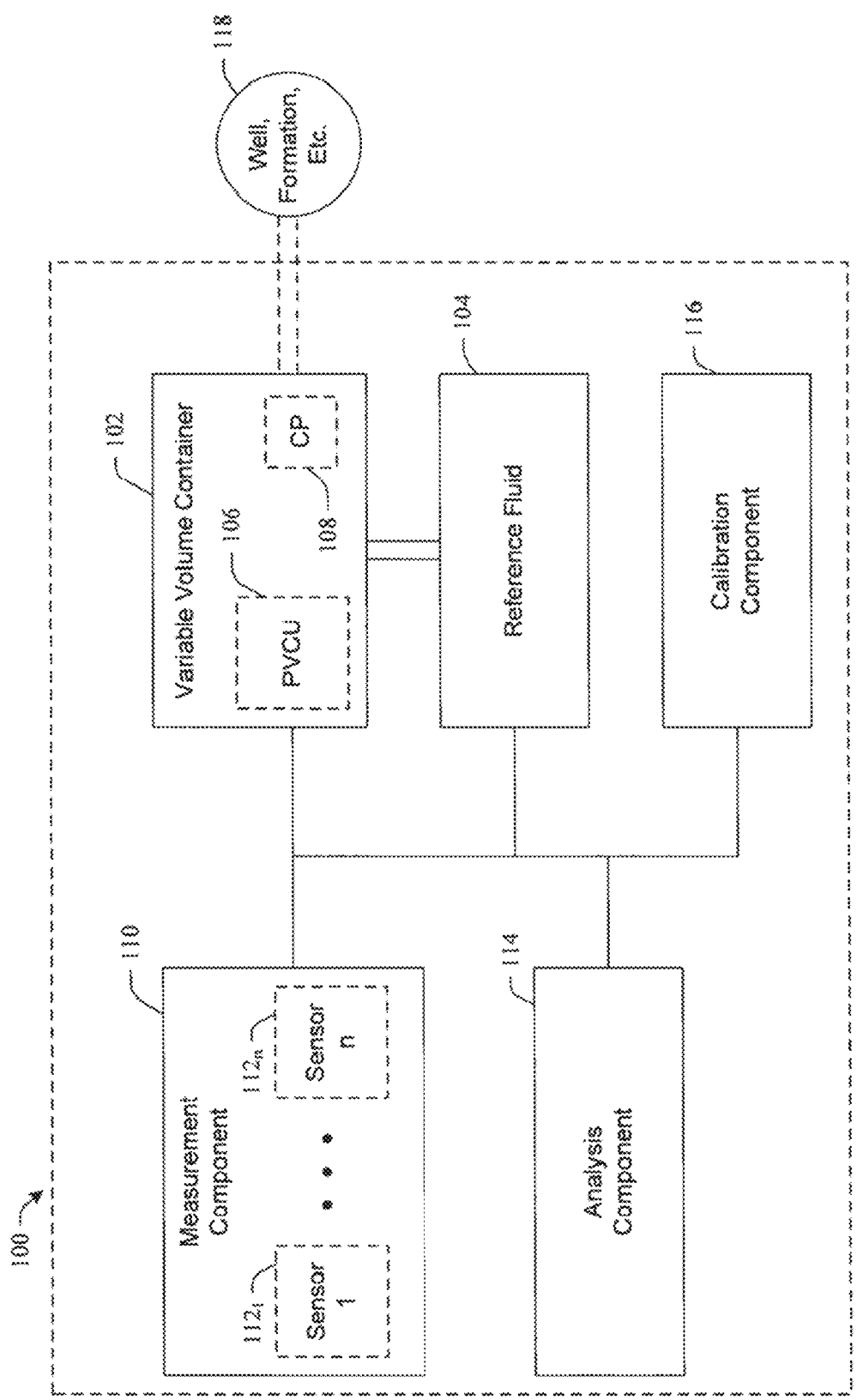
FIG. 1 illustrates at least a portion of a system capable of determining phase behavior and fluid properties of a fluid sample in accordance with aspects of the subject innovation.

The innovation is now described, with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

In some embodiments, the innovation comprises a system capable of making determinations of fluid properties and phase behavior of a fluid sample. The system can be calibrated based on one or more calibration functions to obtain calibrated values of one or more system parameters. These one or more system parameters can be values associated with the system that are not dependent upon which of multiple fluids may be in the system, such as a system volume, dimensions or other characteristics of components of the system (e.g., radius, length, compliance characteristics, etc.), etc., including any dependence on independent variables such as pressure, temperature, etc. Calibrated values of these one or more system parameters can be determined based on one or more calibration functions, which can model the dependence of the one or more parameters on independent variables such as pressure, temperature, etc. These one or more calibration functions can be determined based at least in part on measurements made on a reference fluid having known properties.

In some embodiments, the innovation can comprise a method of calibrating a system capable of determining fluid properties and phase behavior of a fluid sample. One or more system parameters can be calibrated based on measurements taken over a range of values of an independent variable (e.g., pressure, temperature, etc.) In one example, the system can be filled with a reference fluid and the system volume can be contracted (and the reference fluid pressurized). Then the system volume can be expanded (end the reference fluid depressurized) while measurements are taken regarding fluid properties and phase behavior of the reference fluid. One or more system parameters (e.g., a volume of the system, etc.) can be calibrated based at least in part on the measurements and known data regarding the reference fluid. Additionally or alternatively to contracting and expanding the system volume, measurements and calibration can be performed based on changes in a different independent variable (e.g., temperature, etc.). Results or answer products may then be provided based on measurements the system takes of fluid samples and the one or more calibrated system parameters.

In aspects described further herein, these systems and methods may be used to make more accurate measurements of fluid properties and phase behavior in situ in a well drilled in the Earth's crust. These more accurate measurements can be based at least in part on one or more system parameters that can be calibrated, as described herein. Utilizing one or more approaches or techniques described herein, one or more parameters of a system can be calibrated based on properties of a known or reference fluid. In various embodiments of the subject innovation, measurements can be taken with a system calibrated according to techniques or methods described herein to provide more accurate measurements than conventionally available.

As used in this application, the terms "component" and "system" are intended to include, at least in some cases, reference to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Turning to FIG. 1, in one embodiment, the innovation includes a system 100 that is capable of determining phase behavior and fluid properties of a fluid sample in accordance with aspects of the subject innovation. System 100 is capable of being calibrated by techniques described herein to obtain one or more calibrated system parameters. These one or more calibrated system parameters can be used to provide more accurate information regarding the phase behavior and fluid properties of the fluid sample. For phase behavior, the phase-change pressure of captured fluid can be obtained during depressurization (alternatively or additionally, measurements, calibration, and associated results can be based on changes in a different independent variable, such as temperature, etc.). The phase-change pressure can include, for example, the bubble point pressure ($P_b$), dew point pressure ($P_d$), and asphaltene onset pressure (AOP) where applicable. In addition, fluid properties (such as density, viscosity, compressibility, etc.) can be measured with ore derived from sensors in system 100. In various embodiments, some or all of the components of system 100 can be integrated into a single tool or apparatus. In other embodiments, however, some of the components and associated functions (e.g., pressurizing or depressurizing a fluid sample (or, alternatively, altering the temperature of a fluid sample, etc.), taking measurements on the fluid sample, etc.) can be located and/or occur remotely (in whole or in part) from other components and associated functions (e.g., analysis, calibration, etc.). As another example, a sample of a known reference fluid need not be stored inside system 100, although it can be in some implementations (e.g., it may facilitate calibration that can occur in situ, periodically, etc.).

System 100 can include a variable volume container 102 capable of storing, a fluid during measurements and further capable of altering the pressure of the fluid in variable volume container 102. The fluid in variable volume container 102 can vary, depending on procedures that are being applied by system 100. For example, in a calibration procedure, a reference fluid 104 can be used as the fluid in variable volume container 102. In another example, for a test procedure, a fluid sample with properties and behavior that are to be determined can be used as the fluid in variable volume container 102. Alternatively, both procedures can be performed sequentially.

Variable volume container 102 can be substantially any container with a volume variation mechanism (e.g., at least one of a motor, moveable valve, etc., to at least one of pressurize or depressurize a fluid in variable volume container 102). Examples of containers that can be used as variable volume container 102 are laboratory sample containers, sample bottles, sample cells and other laboratory testing apparatuses, field testing equipment, etc., provided that there is an associated volume variation mechanism. In a petroleum setting, examples include sample containers or sample bottles used in a PVT (pressure, volume, and temperature) laboratory, containers or flow lines (or portions thereof) in well logging, tools such as wireline tools or logging while drilling (LWD) tools, etc. in aspects, variable volume container 102 can comprise a pressure volume control unit (PVCU) 106 that can depressurize the fluid in variable volume container 102, for example by having an expandable volume (e.g., via a moveable piston). In aspects, variable volume container 102 can also optionally comprise circulating pump 108, which can at least one of mix or agitate the fluid such that phase changes (e.g., bubble formation) can be more readily detected by sensors. In other aspects, variable volume container 102 can comprise a temperature control unit (not shown) to alter the temperature (by substantially any means known in the art) of a fluid in variable volume container 102.

In aspects, reference fluid 104 can be selected as a fluid that has at least one of well-known or precisely defined characteristics (such as phase behavior and fluid properties), for example, in a pressure-volume region of interest based on tests to be conducted on a fluid sample. For example, reference fluid 104 can be selected as a fluid for which widely accepted reference data is available or known properties can otherwise be obtained, for example, in the National Institute of Standards and Technology's (NIST's) REFPROP (Reference Fluid Thermodynamic and Transport Properties Database); or can be a fluid for which known properties can be obtained through some other means (e.g., reliable measurements in a PVT laboratory, etc.). In various examples discussed herein, examples of reference fluids are discussed (e.g., toluene, heptanes, etc.). However, these examples are intended merely to illustrate the principles discussed herein, and not to limit the types of reference fluids that can be selected.

Additionally, system 100 can include a measurement component 110 that comprises one or more sensors $112_1$ to $112_n$. Measurement component 110 can obtain data related to characteristics such as phase behavior (including phase change pressure, e.g., $P_b$, $P_d$, AOP, etc.), and fluid properties (e.g., density, viscosity, pressure, etc.). This data can be obtained as variable volume container 102 at least one of pressurizes or depressurizes the fluid, or additionally (e.g., sequentially) or alternatively, based on changes in one or more other independent variables, such as temperature, etc. The one or more sensors $112_1$ to $112_n$ can include any of a variety of sensors used for obtaining fluid properties or phase behavior, including but not limited to those discussed herein, for example, pressure and/or temperature sensors (e.g., a silicon-en-insulator (SOI) gauge, etc.), density and/or viscosity sensors (e.g., a density/viscosity (DV) rod (based on the principle of mechanically vibrating and resonating elements interacting with the fluid), vibrating wire sensor, etc), sensors to detect phase change during depressurization, temperature change, etc. (e.g., a spectrometer such as a single channel spectrometer, etc.), acoustic sensors, fluorescence/reflectance sensor, multi-channel spectrometer, backscattering sensors, resonating piezoelectric crystal sensors, micro electro-mechanical systems (MEMS) sensors, etc. By taking a plurality of measurements as pressure changes, data showing the above characteristics as a function of time can be collected. In some aspects, one or more additional or redundant sensors can be included as a form of quality control to cross-validate the techniques of the subject innovation, as described further herein. For example, for calibrations related to determining a volume, a density sensor can be included to verify or determine that a mass calculated based on that volume remains constant. Such a determination can be used either as quality control to ensure the accuracy of a calibration of one or more system parameters (e.g., volume), or to monitor whether or not system 100 has one or more leaks.

Additionally, system 100 can further include an analysis component 114 that can analyze data collected by measurement component 110 and the one or more sensors $112_1$ to $112_n$. Based on analyzing this data, analysis component 114 can produce one or more answer products based at least in part on the analyzed data. These answer products can include, for example, density as a function of pressure, viscosity as a function of pressure, compressibility as a function of pressure, or phase pressure (e.g., $P_b$, $P_d$, AOP, etc.). Additionally, analysis component 114 can coordinate with calibration component 116 to provide answer products based at least in pan on the analyzed data and one or more calibrated system parameters. These calibrated system parameters can be based at least in part on measurements obtained of a reference fluid and on one or more calibration functions determined by calibration component 116, as discussed herein. In aspects, analysis component can determine one or more of answer products based on one or more models, such as a rigid model or one or more calibrated models as described herein.

Calibration component 116 can be used to calibrate one or more parameters of system 100 to enable system 100 to provide more accurate data on fluid properties and phase behavior. Calibration component 116 can determine one or more calibration functions that can be used to obtain calibrated values for one or more system parameters. These calibrated values of system parameters can be used to adjust raw data obtained by measurement component 110 or answer products determined by analysis component 114. The one or more calibration functions can adjust the system parameters used to obtain the data or answer products to better correspond to actual properties of a fluid.

For a variety of reasons, data obtained from measurements on a fluid in a variable volume container (such as variable volume container 102) can differ from actual values. As an example, traditional systems and methods frequently use idealized models, such as assuming a rigid model of the system (e.g., assuming the walls of the variable volume container, seals, etc. are rigid) for the determination of the system volume, without taking the finite compliance inverse of rigidity) of surrounding material into account. However, various portions of the system (e.g., seals, etc.) can be deformed under pressure, rendering a rigid model insufficient to account for the volume when the system is under pressure. Additional sources of error can arise from any of a number of sources, such as variations in components (e.g., based on factory tolerances, over a lifespan, etc.), measurement inaccuracies (e.g., that may be biased more in one direction than another), additional 'idealized' approximations, etc. In general, these sources of error could vary between different instances of the same system. Instead of an idealized model for various system parameters (e.g., volume, etc.), these models can be modified to obtain one or more calibrated models, which can include one or more unknown functions that corresponds to the various 'real-world' effects (e.g., finite compliance, etc.) that make components of the system 100, such as the variable volume container 102, differ from an ideal model.

In aspects, calibration component 116 can determine the one or more calibration functions via a calibration procedure. In such a calibration procedure, variable volume container 102 can be filled with reference fluid 104 and can have one or more independent variables (e.g., pressure, temperature, etc.) altered (e.g., have the pressure or the temperature increase or decrease, etc.) as during testing, of a fluid sample, while measurement component 110 and one or more sensors $112_1$ to $112_n$ can obtain data on reference fluid 104. In aspects involving changes in pressure, after contracting variable volume container 102 but before expansion, variable volume container 102 can be monitored at constant pressure for a period of time (e.g., 10-15 minutes or more, etc.) to monitor for the presence of leaks. Similar monitoring can be performed if a different independent variable is selected to be altered. Based on the data obtained, analysis component 114 can determine one or more answer products. Based on these one or more answer products, calibration component 116 can compare at least one of the data obtained or the one or more answer products to known data regarding the fluid properties and phase behavior of reference fluid 104 (e.g., in NIST REFPROP, based on independent measurements such as in a PVT laboratory, etc.). Based on the comparison, calibration component 116 can determine one or more calibration functions that approximate the unknown functions in one or more calibrated models. The one or more calibration functions can approximate the unknown function by a series approximation, curve fitting, etc. Based on the one or more calibration functions, one or more system parameters e.g., volume, etc.) can be calibrated to obtain results or answer products that correspond to known data regarding the fluid properties and phase behavior of reference fluid 104 (e.g., in NIST REFPROP, based on independent measurements such as in a PVT laboratory, etc.).

In some aspects, calibration functions can be revised to be more accurate based on various factors, such as the extent to which a system parameter as calibrated by a calibration function fits the data obtained or the one or more answer products to known data (e.g., as measured by regression analysis techniques, such as least squares, Bayesian methods, etc.) regarding the fluid properties and phase behavior of reference fluid 104 (e.g., in NIST REFPROP, based on independent measurements such as in a PVT laboratory, etc.). Optionally, if a best fit calibration function does not bring the data obtained or the one or more answer products to within a threshold of known data (e.g., based on the results of regression analysis, the value of a chi-square error, etc.), a more accurate calibration function can be selected instead. For example, if a regression analysis (e.g., least squares analysis, etc.) determines that data or answer products based on a system parameter calibrated with a best fit quadratic calibration function has a measure of fitness (e.g., the sum of the squares of the errors in a least squares method) above a threshold, a best fit cubic equation can be used instead. More accurate approximations can be repeatedly selected until a measure of fitness meeting the threshold is found.

The one or more calibration functions determined by calibration component 116 during a calibration procedure can be stored for later use. During a test procedure, variable volume container 102 can be filled with a fluid sample for which data is to be obtained. Variable volume container 102 can be contracted and expanded (or, alternatively or additionally, have one or more other independent variables (e.g., temperature, etc.) altered), while measurement component 110 and one or more sensors $112_1$ to $112_n$ can obtain data on the fluid sample. Based on the data obtained, analysis component 114 can determine one or more answer products. Calibration component 116 can determine the measured data or the one or more answer products based at least in part on one or more calibrated values of system parameters, as calibrated by the one or more calibration functions (e.g., as determined during a calibration procedure).

Additionally, as explained elsewhere, one or more of sensors $112_1$ to $112_n$ can be included, to at least one of perform quality control or validate the calibration. For example, if data is obtained on both the density of the fluid and the volume of variable volume container 102 (e.g., as a function of pressure, temperature, etc.), the total mass of the fluid in variable volume container 102 should remain constant (e.g., as a function of pressure, temperature, etc.), and the extent to which it remains constant (e.g., as measured by regression analysis such as least squares, Bayesian methods, etc.) can be used to refine the model, by selecting a more accurate calibration function as needed. Alternatively or additionally, in a calibrated system 100, measurements of the total mass of fluid in variable volume container 102 can be used to detect the presence of leaks.

System 100 can be implemented in a variety of settings to obtain data on the fluid properties or phase behavior of a fluid sample. System 100 can be used in a laboratory setting, such as a PVT laboratory, etc. Additionally, system 100 can be used for well logging (e.g., to make measurements or a record of measurements related to materials penetrated by a borehole, etc.), including measuring fluid properties and phase behavior in situ (e.g., in petroleum or natural gas applications, etc.). In well logging applications, various embodiments of system 100 can be used as wireline tools (e.g., by lowering the system or portions thereof into a borehole after drilling is completed, etc.). In other aspects related to well logging, some embodiments of system 100 can be used as a measurement while drilling, (MWD) tools, logging while drilling (LWD) tools, or any other types of drill string downhole tools (e.g., by incorporating the system or portions thereof into a drill collar, other portions of the bottom hole assembly, etc.). In such well logging applications, system 100 can be connected to and obtain fluid samples from a borehole or well, formation, etc. 118.

What follows is a more detailed discussion of systems, methods, and apparatuses associated with specific embodiments and aspects of the subject innovation. To aid in the understanding of aspects of the subject innovation, theoretical analysis and experimental results associated with specific experiments that were conducted are discussed herein. However, although for the purposes of obtaining the results discussed herein, specific choices were made as to the selection of various aspects of the experiments and associated setups—such as choice of calibration methods (e.g., polynomial curve fitting with least squares regression, etc.), design and application of device (e.g., petroleum well logging, etc.), the setting in which the device is employed (e.g., as a wireline tool, a logging while drilling tool, etc.), as well as other aspects—the systems and methods described herein can be employed in other contexts, as well. For example, aspects of the subject innovation can be utilized to determine fluid properties and phase behavior of a fluid sample, independent of the ultimate application of those devices. In another example, systems discussed herein could be constructed with different choices of sensor elements than those used in the experiments discussed herein, and may have differing configurations, as explained in greater detail herein.

The experiments and associated results discussed herein were conducted and obtained with an experimental downhole module, although other types of tools and systems could be used in connection with the subject innovation.

The experimental downhole module is combinable with other modules of a wireline modular dynamics tester (MDT) and is capable of capturing the fluid sample and measuring its phase behavior and fluid properties using sensors located along the flow line. For phase behavior, the phase-change pressure of captured fluid can be obtained during depressurization (alternatively or additionally, a phase change temperature, etc. can be determined based on altering the temperature, etc.). The phase-change pressure can include the bubble point pressure ($P_b$), dew point pressure ($P_d$) and asphaltene onset pressure (AOP) of reservoir fluid, wherever applicable. In addition, the fluid properties such as density, viscosity, compressibility, etc., can be measured in situ with the sensors in the system. Traditionally, these phase-change pressures (temperatures, etc.) and fluid properties have been measured in the PVT laboratory using the reservoir fluid captured in a sample bottle. With a well logging tool such as described herein, these phase-change pressures (temperatures, etc.) and fluid properties can be monitored and measured downhole in reservoir conditions.

The systems, methods, and techniques discussed herein can be used for conducting an in situ calibration of well logging tools, as explained in connection with the following experimental results. However, these systems, methods, and techniques can also be used in other aspects of the subject innovation, although corresponding results (e.g., calibration functions, measured data, etc.) may vary accordingly. However, a person of skill in the art would understand, based on the discussion herein, how to adapt these systems, methods, and techniques to the various aspects of the subject innovation.

The calibration procedure experiment included pre-filling the flow line of the experimental downhole module with a known fluid, such as reference fluid 104. This in situ calibration (e.g., "in situ" in that the procedure was conducted with the known fluid filled in place in the flow line) provided the ability to check and cross-validate the measurements, enabling the opportunity to ensure the sensors and system worked in a consistent and predictable manner prior to performing downhole fluid tests. The calibration procedure can be conducted with the tool (e.g., wireline, LWD, etc.) in a shop or with the tool running into the borehole. The results of calibration can subsequently be used to obtain answer products of unknown reservoir fluid and to detect anomalies (e.g., leaks) that may have occurred in the system.

Figure 2:
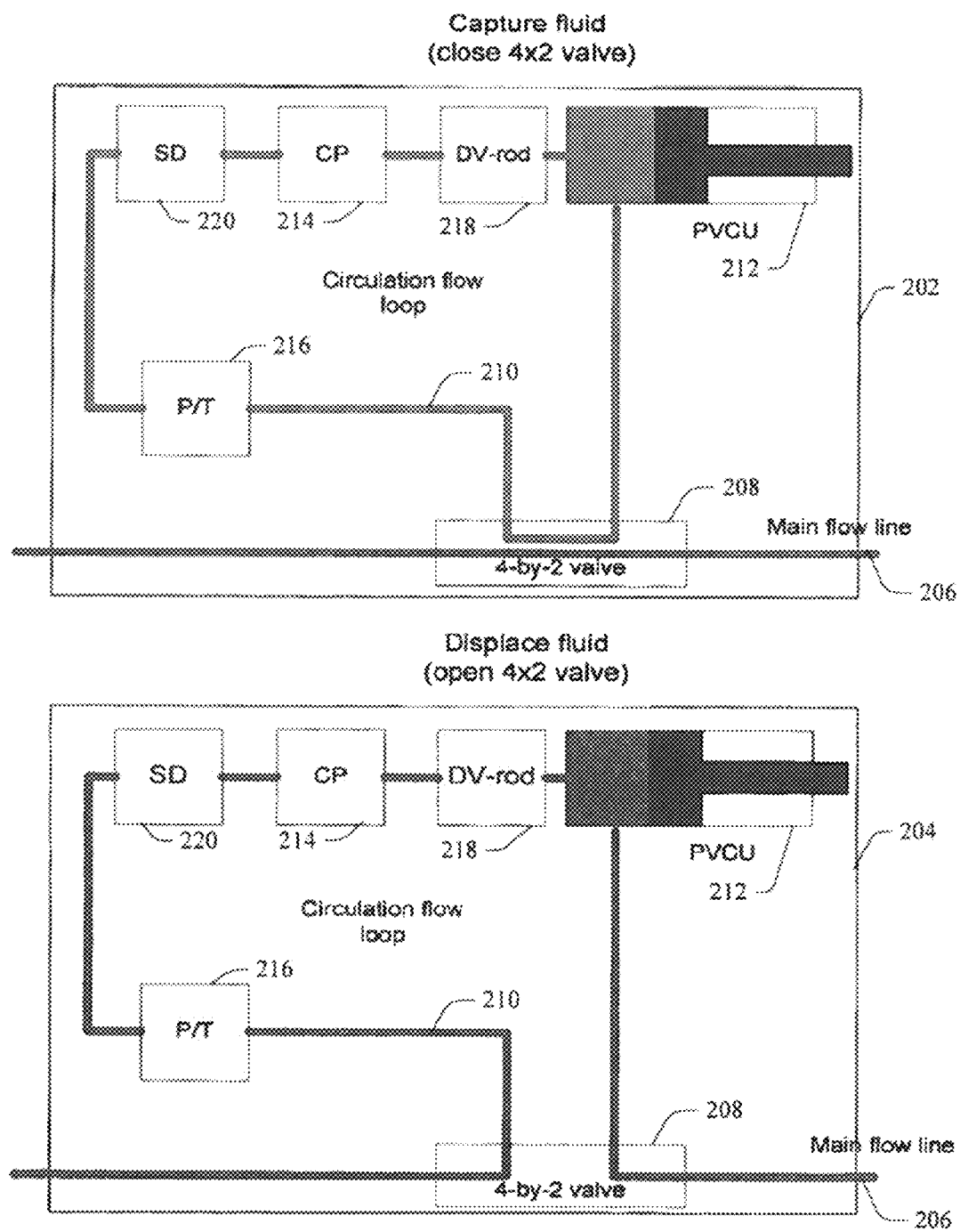
FIG. 2 shows a diagram of an instrumented variable volume container in two different configurations that is capable of being implemented in a wireline or logging while drilling (LWD) tool.

Turning to FIG. 2, shown is a functional diagram of the experimental downhole module in two different configurations, a fluid capture configuration 202 and a fluid displacement configuration 204. Main flow line 206 shown at the bottom can transport the reservoir fluid entering from the right and exiting to the left. The 4-by-2 valve (i.e., 4 port-2 position valve) 208 controls the flow in the module. When it is in the closed position, as in configuration 202, the fluid in circulation flow loop 210 can be separated and isolated from main flow line 206. In contrast, when in the open position, as in configuration 204, the reservoir fluid can be diverted through circulation flow loop 210 to displace the existing fluid in the loop.

The fluid sample captured in circulation flow loop 210 can undergo a depressurization by expanding the volume of the flow loop 210 by using the pressure-volume control unit (PVCU) 212. During depressurization, circulating pump (CP) 214 in loop 210 can be used to help mix and/or agitate the fluid so that any phase changes (e.g., bubble formation) can be "seen" by all sensors. The accuracy of phase behavior measurements can be improved with the mixing and agitating of fluid during the depressurization. Other sensors along the circulation flow loop can include (1) a silicon-on-insulator (SOI) gauge 216 for measuring the pressure and temperature (P/T), (2) density/viscosity (DV)-rod 218 for measuring the fluid density and viscosity, and (3) optical scattering detector (SO) 220, which can be a single channel spectrometer used to detect the fluid phase change during depressurization.

The measurements acquired during the depressurization can consist of: (1) Pressure p(t) and temperate T(t) vs. time t from SOI gauge 216, (2) Viscosity and density vs. time from DV-rod 218, (3) Scattering detector response vs. time from scattering detector 220, and (4) Depressurization rate and idealized volume variation v(t) vs. time. The idealized volume variations can be measured for example via the measurement of a rotation of a motor actuating a piston in the PVCU 212.

Note that usual graphical representations do not use time t on the x-axis, but the pressure p(i). An example graphical representation is the cross plot of the idealized volume variation v(t) against the pressure p(t). For simplicity, this cross plot is herein referred to as v(p) instead of v(p(t)), Similar simplified notation are used herein for measurements other than the idealized volume variation v.

From these fundamental measurements, the following answer products can potentially be provided: (1) Density vs. pressure, (2) Viscosity vs. pressure, (3) Compressibility vs. pressure, and (4) Phase pressure (which, depending on the fluid, can include one or more of: asphaltene onset pressure, bubble point pressure, or dew point pressure).

Alternatively or additionally, a different independent variable can be selected temperature, etc.), and measurements and corresponding answer products can be determined based on variations in that independent variable over a range.

Note that the depressurization operation of the experimental downhole module is not the same as the constant composition expansion (CCE) performed in a PVT laboratory. In a PVT laboratory, the bubble point can be determined by a CCE. A known volume of fluid sample can be depressurized from a pressure greater than or equal to the reservoir pressure at the reservoir temperature. At each step that the pressure is reduced, the fluid sample can be allowed to come to equilibrium by agitating with the mixer. Once the sample has come to equilibrium, the pressure and volume can be recorded. This depressurization process can repeat at intervals of 500 or 1000 psi until the gas is separated from the fluid sample. After the gas is separated from the liquid, the depressurization step can be reduced to a smaller increment such as 100 psi. The entire process can take a few hours to complete for a regular oil sample, whereas it can take a few days for heavy oil. The bubble point can be determined as the break point between the single phase and two-phase region based on the pressure and volume data recorded, or by the visual observation of formation of bubbles in the fluid. As opposed to this laboratory procedure, well logging tools can undergo a continuous volume expansion with circulation, whereas the PVT lab performs a step-wise depressurization and waits for the equilibrium state (by agitating the fluid with the mixer) at each discrete pressure step. In essence, the experimental downhole module and similar tools can conduct a PVT (pressure-volume-temperature) analysis downhole at reservoir conditions. The volume of fluid in the system, however, cannot be determined accurately and as a result, the fluid compressibility derived from the PV data can be difficult to obtain.

Conventionally, the isothermal compressibility of a fluid is defined in terms of the pressure-volume (PV) relationship as follows:

$$c(p) = -\frac{1}{V(p)} \frac{dV(p)}{dp} \quad (1)$$

where "c(p)" is the compressibility of the fluid, "V(p)" is the volume and "p" is the pressure of the fluid. The volume in equation (1) is a function of pressure (i.e., V(p)) during depressurization (or pressurization) and the compressibility of the fluid is also a function of pressure (i.e., c(p)) with the units of $psi^{-1}$.

Traditional, idealized models would suggest that the total volume, V(p), during depressurization is equal to the volume of loop flow line 210 plus the volume expanded by PVCU 212, i.e.:

$$V(p) = V_0 + v \quad (2)$$

where $V_0$ is the volume of loop flow line 210 and v(p) is the idealized volume variation as function of pressure p(t). This, however, represents a rigid model without taking the finite compliance of surrounding material into account. For well logging tools, loop flow line 230 and PVCU 212 are made of material with finite compliance and along loop flow line 210 there are multiple elastomeric seals that can be deformed under pressure. Therefore, a rigid model is insufficient to account for the total volume when the system is under pressure. Accordingly, in aspects, the subject innovation adds a correction term to equation (2):

$$V(p) = V_0 + v(p) + f(p) \quad (3)$$

where $f(p)$ is an unknown function of pressure p, to account for extra volume expansion due to the exertion of pressure upon the surrounding medium. The extra volume expansion due to pressure can be caused by the finite compliance of material made up for the system. $V_0$ in equation (3) can, therefore, be interpreted as the volume of loop flow line 210 when the pressure is equal to zero.

The unknown function, $f(p)$, can be approximated to any necessary or desired degree of precision by a series approximation (e.g., Taylor or Maclaurin. Laurent, trigonometric, etc.). By including a finite number of terms of the series, the necessary or desired degree of precision can be obtained by determining suitable values for the coefficients, as described herein. For example, by including the first n terms of a Taylor series, $f(p)$ can be approximated by an nth degree polynomial (e.g., a Taylor polynomial). Alternatively, curve fitting methods can be used to obtain an approximation of the unknown term, such as by finding a best fit polynomial of nth degree. Additional terms can be included in either technique in order to obtain greater accuracy. In an example with n=2, equation (3) would become:

$$V(p) = V_0 + v(p) + \alpha p + \beta p^2 \quad (4)$$

where "α" and "β" are unknown coefficients of a 2nd degree polynomial (i.e., quadratic) approximation to the unknown function $f(p)$ that can account for extra volume expansion due to the exertion of pressure upon the surrounding medium. The "α"-term in equation (4) is a linear volume correction with respect to pressure, whereas the "β"-term corresponds to the quadratic volume correction with respect to pressure. Although a quadratic approximation to an unknown function of volume is discussed herein in order to provide a specific illustration of the principles of the subject innovation, other approximations (e.g., other degrees of polynomials, non-polynomial functions, etc.) can be utilized, and in aspects, unknown variations or errors in other parameters than volume can be approximated.

In order to obtain the unknown constants "α" and "β" in equation (4), a calibration procedure such as the following can be conducted. First, loop flow line 210 can be filled with a known fluid toluene, etc.) such as reference fluid 104 and pressurized to a high pressure. Then, the known fluid can be depressurized by expanding the volume of PVCU 212 (e.g., by withdrawing a piston of PVCU). During this process, the pressure data $p_i$ and the expanded volume $v(p_i)$ can be recorded, where "i" denotes the recorded index. The final step of calibration involves finding any unknown constants or coefficients, which in the illustrative example, would involve finding "α" and "β" so that the compressibility computed from the recorded data matches the compressibility profile of known fluid. In the specific quadratic example discussed herein, the compressibility computed from the recorded data is:

$$c(p_i) = -\frac{1}{V(p)} \frac{dV(p)}{dp}\bigg|_{p=p_i} = \\ -\frac{1}{V_0 + v(p) + \alpha p + \beta p^2} \left( \frac{dv(p)}{dp}\bigg|_{p=p_i} + \alpha + 2\beta p_i \right) \quad (5)$$

However, with other approximations, the form of the right hand side would vary accordingly. For example, if the unknown function were approximated by a cubic with unknown coefficients γ, δ, and δ (e.g., approximating $f(p)$ with $\gamma p + \delta p^2 + \epsilon p^3$), the $\alpha p + \beta p^2$ term would be replaced with $\gamma p + \delta p^2 + \epsilon p^3$, and the $\alpha + 2\beta p_i$ would be replaced with $\gamma + 2\delta p_i + 3\epsilon p_i^2$. A person of skill in the art would understand, in view of the discussion herein, other variations that are also within the scope of the subject disclosure e.g., nth degree polynomials, non-polynomial functions, etc.).

In equation (5), the derivative of v(p) with respect to p can be computed numerically from the recorded data p(t) and v(t). To match the known fluid compressibility profile, regression analysis can be used. In an example employing a least-squares method with two unknowns (the quadratic approximation discussed above), the following least-squares inversion problem can be solved:

$$\min_{\alpha,\beta} \sum_i (c(p_i) - c_{known}(p_i))^2 / \zeta \quad (6)$$

Where $c_{known}(p_i)$ is the known fluid compressibility and the summation can be done over all recorded pressures in the depressurization step (or, alternatively, over a region of interest among the recorded pressures, if a better fit to that region is more useful or needed for a particular application), and is the number of degrees of freedom for fitting data. For a different number of unknowns, a minimum of the corresponding sum would need to be found over all of the unknowns.

Note that the sum of squares of the deviation in equation (6) is closely related to the goodness-of-fit statistic called chi-square (or $\lambda^2$). The minimization problem of equation (6) can be solved in a variety of manners, for example, by a nonlinear regression procedure such as the Levertberg-Marquardt algorithm, or, alternatively, by a two-dimensional search (or, in the case of a different approximation involving n unknowns, by an n-dimensional search), etc. In the specific example, given a range of possible values of "α" and "β", one can compute the chi-square errors for each pair of "α" and "β", i.e.

$$\sum_i (c(p_i) - c_{known}(p_i))^2 / \zeta \qquad (7)$$

and displays the errors as a function of "α" and "β" values. The optimal "α" and "β" can then be identified from the minimum of 2D display (or n-dimensional display, chart, array, etc., when there are n unknowns).

Although the forgoing analysis focused on the compressibility and changes in volume based on variations in pressure, in aspects of the subject innovation, volume can be calibrated based on other independent variables (e.g., temperature, etc.), or one or more other system parameters (e.g., the dimensions, damping, or other characteristics of a vibrating wire sensor, etc.) can be calibrated based on pressure, temperature, etc. These calibrations can still be based on approximations to unknown functions, although the specific equations and functions would vary based on the corresponding changes in choice of parameter and/or independent variable, as would be known to person of skill in the art in light of the subject discussion. For example, changes in volume based on temperature would not depend on the compressibility, but rather the thermal expansion $$\left(\text{i.e., } \frac{1}{V(T)} \frac{dV(T)}{dT}\right),$$

and an approximation of the thermal expansion of the system would be a volume as a function of temperature (e.g., a quadratic approximation would be of the form $\alpha T + \beta T^2$, etc.). Calibration can be based on one or more independent variables (e.g., pressure, temperature, etc.), and calibration of a system parameter based on two or more can occur sequentially (e.g., with a first set of measurements taken during an isothermal pressurization and depressurization of a reference fluid, a second set of measurements taken during an isobaric temperature change of the reference fluid, etc.).

Additionally, the system can be checked for leaks prior to implementing the calibration procedure described above. With a system leak, recorded data would still be able to fit the model of equation (3). However, mixing of known fluid and a leaking fluid (e.g., mud, J26, etc.) from outside can alter the known fluid properties, which has the potential to render the calibration results invalid.

The methods and techniques described herein were demonstrated using data recorded in testing with the experimental downhole module. In a first test, the loop flow line was initially filled with toluene, which was subsequently displaced by medium oil. The first test was conducted at the temperature of 80° C. and a maximum pressure of 10 kpsi. The known or reference) toluene compressibility (as a function of pressure) at 80° C. was obtained from the National Institute of Standards and Technology's (NIST's) REFPROP (Reference Fluid Thermodynamic and Transport Properties Database), Prior to the test, the hypersolve (lab cleaning fluid) was used to measure the volume of loop flow line 210, which was about 56 cc (i.e., $V_0$) at room temperature and pressure.

Figure 3:
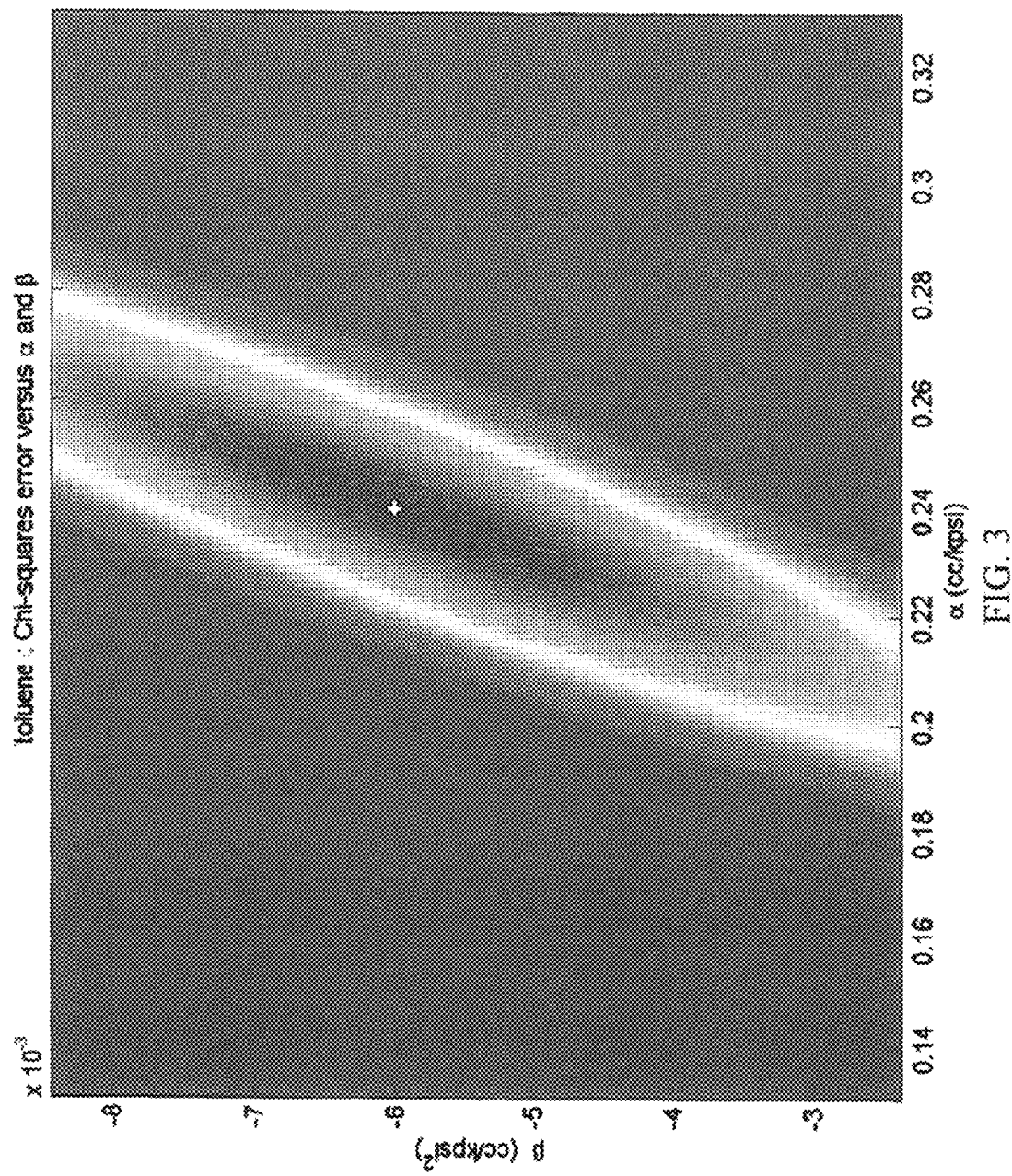
FIG. 3 shows a 2D display of computed chi-square errors between reference and test data related to toluene compressibility.
Figure 4:
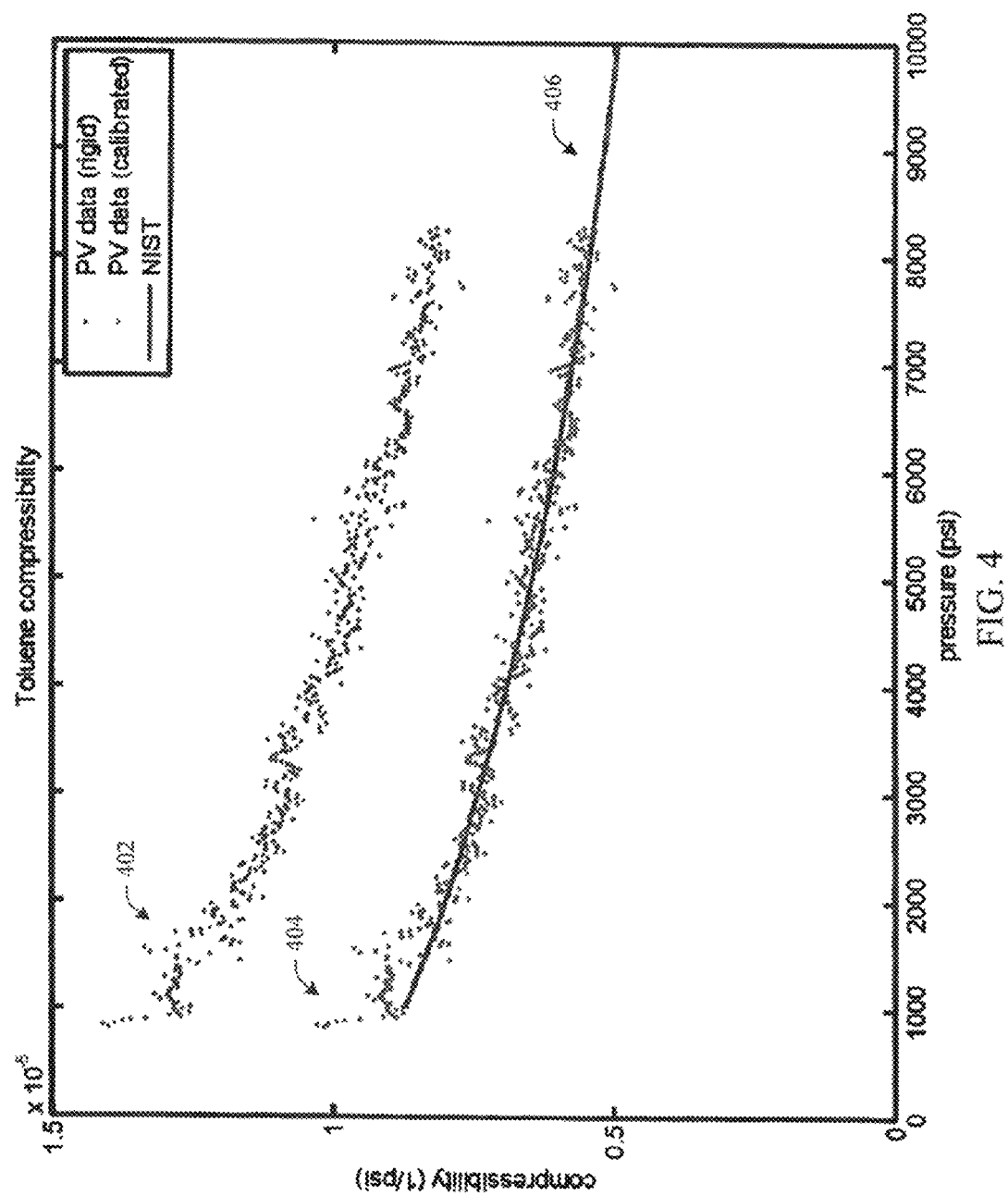
FIG. 4 shows the comparison of computed and reference toluene compressibility profiles at 80° C.

FIG. 3 shows the 2D display of computed chi-square errors in the first test, based on the recorded data, the volume model of equation (4) using a second order polynomial approximation), and the reference toluene compressibility. The minimum of chi-square errors (as a function of u and occurred at about $\alpha=0.24$ cc/kpsi and $\beta=-6.0$ e–3 cc/kpsi$^2$. FIG. 4 shows the comparison of computed and reference toluene compressibility profiles. The green dots 402 represent the computed compressibility profile obtained with the recorded data and the rigid volume model of equation (2), whereas the red dots 404 represented the compressibility profile obtained with the recorded data and the calibrated Model of equation (4), using $\alpha=0.24$ cc/kpsi and $\beta=-6.0$ e–3 cc/kpsi$^2$. The blue curve 406 is the reference compressibility profile from NIST REFPROP. As is clear from FIG. 4, the fluid compressibility based on the rigid model is significantly off from the reference profile, whereas the fluid compressibility based on calibrated model is in very good agreement with the reference profile.

Figure 5:
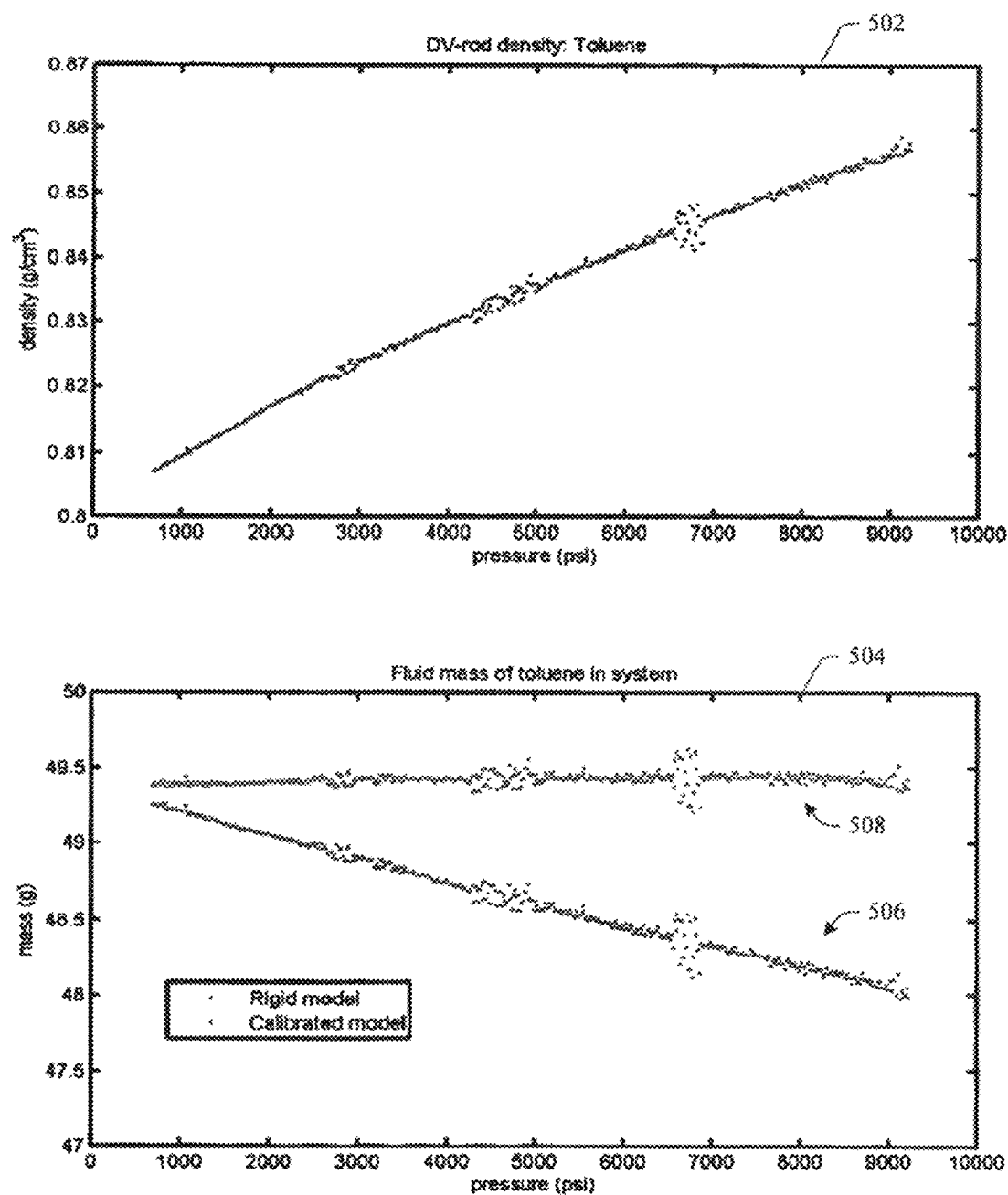
FIG. 5 shows density and mass plots of toluene at 80° C. that can be used for cross validation or consistency check of a system calibration at 80° C.

Additionally, one or more consistency checks for the calibration results described above can be achieved with other sensor measurements along loop flow line 210. As one example, density data from DV-rod 218 was used for this validation. During depressurization, 4-by-2 valve 208 was closed and the fluid was captured in a closed system. The system can be checked beforehand for leaks. For example, checking for system leaks can be conducted while holding the pressure in loop flow line 210 at a different pressure from the main flow line for a lengthy period of time (e.g., 10-15 minutes or more, etc.), where any trend of pressure change within this period can be a possible indication of system leak, etc. If the system does not leak, the mass of captured fluid should remain as a constant during depressurization, changes in temperature, etc. (i.e., conservation of mass). With the calibrated volume available, the mass of fluid was calculated using density measurements from DV-rod 218. FIG. 5 shows the DV-rod density of toluene at plot 502 and the computed mass at plot 504 in the system during depressurization. With the rigid volume model of equation (2), the computed mass (i.e., green dots) 506 showed a systematic decreasing trend with increasing pressure. In contrast, the computed mass 508 with the calibrated model of equation (4) (i.e., red dots) was nearly a constant over the entire pressure range, which is consistent with the conservation of mass in a closed system. Therefore, once it is calibrated and established, the calibrated volume model can be used to detect anomalies such as system leaks, while conducting fluid measurements in the system, whether that be in a lab, downhole (e.g., in a wireline or LWD implementation, etc.), etc. This is because any deviation trend of computed mass (using the calibrated model) from a constant value during depressurization (or changes in temperature, etc.) is possibly indicative of system leaks.

Figure 6:
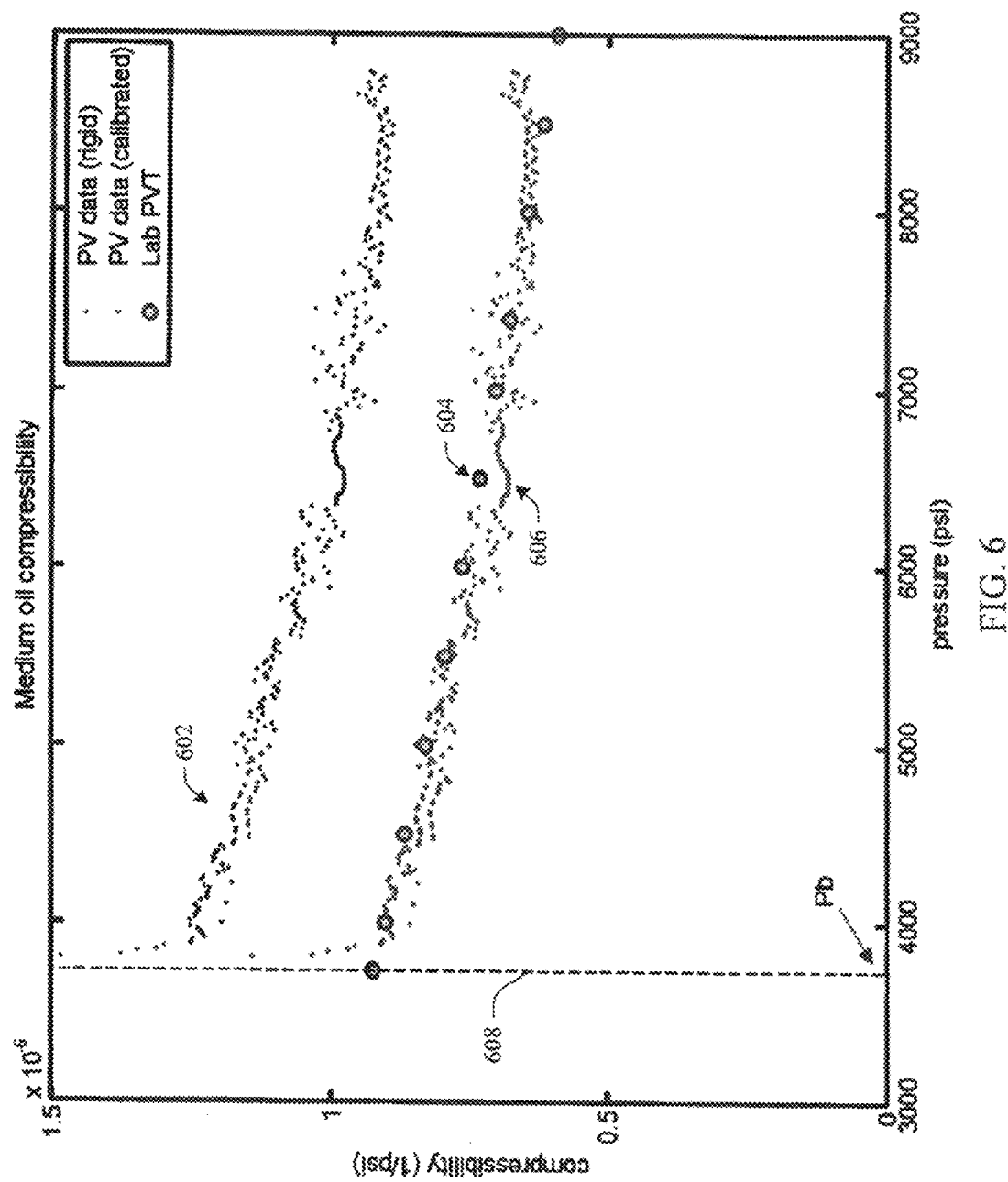
FIG. 6 shows a comparison of computed in situ and laboratory compressibility profiles of medium oil at 80° C.

In a second portion of the first test, the toluene in was eventually replaced by medium oil. FIG. 6 shows a comparison of three compressibility profiles of medium oil computed based on two models implementing data obtained, as compared with results obtained in a PVT laboratory. Using the PV data acquired from the depressurization of medium oil, the compressibility of medium oil was computed. Compressibility profile 602 derived from the rigid model (i.e., green dots) was offset from PVT compressibility profile 604 (i.e., blue circles) by about 30-40%. However, compressibility profile 606, using results derived from the calibrated model of equation (4) (i.e., red dots, using $\alpha=0.24$ cc/kpsi and $\beta=-6.0$ e–3 cc/kpsi$^2$) agreed well with PVT compressibility profile 604. Dotted line 608 indicates the bubble point pressure of medium oil.

Figure 7:
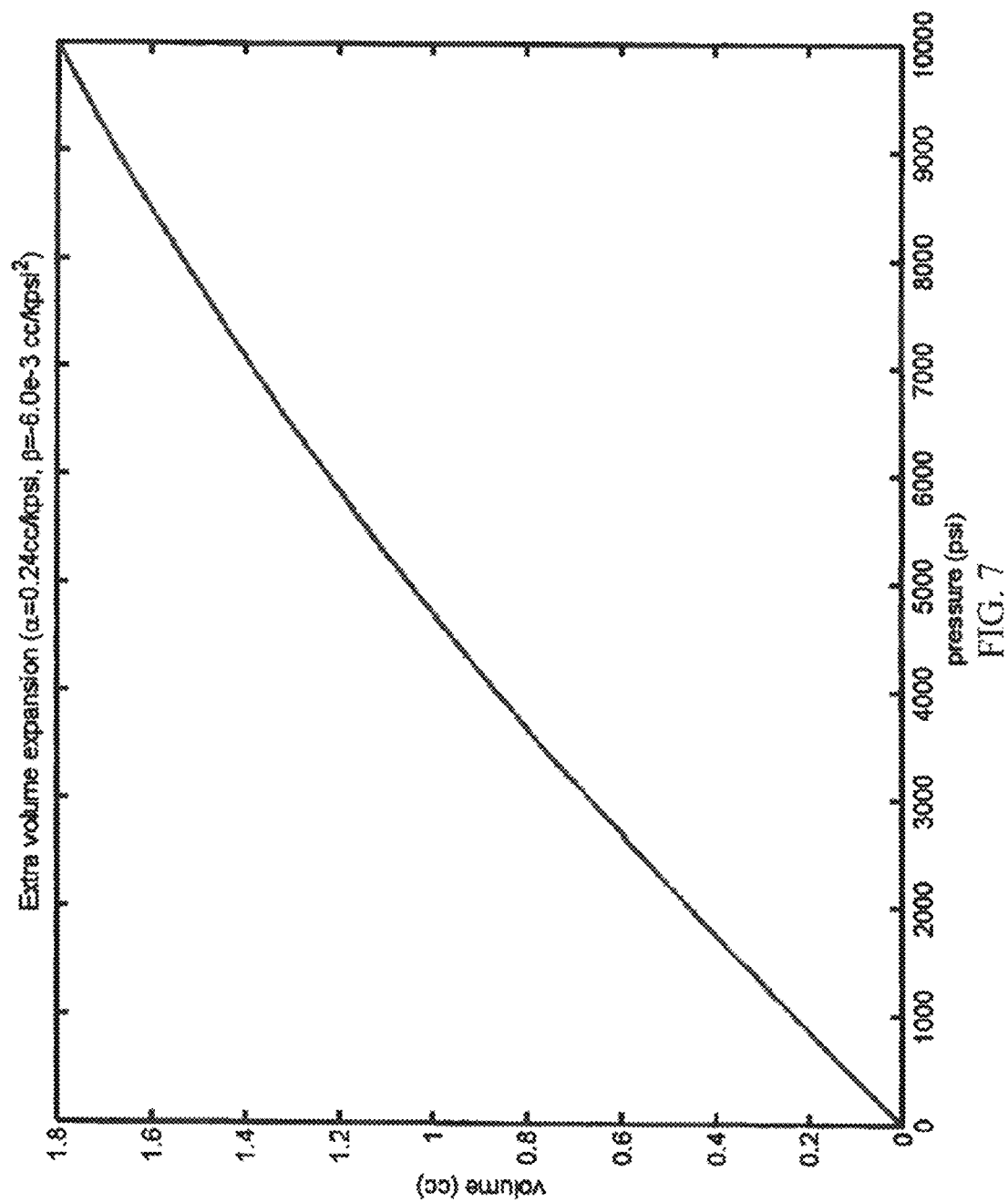
FIG. 7 illustrates the extra volume expansion caused by pressure.

Illustrated in FIG. 7 is the extra volume expansion caused by pressure (i.e., $\alpha p + \beta p^2$) based on the calibrated model of equation (4), with $\alpha=0.24$ cc/kpsi and $\beta=-6.0$ e–3 cc/kpsi$^2$. At the highest pressure (i.e., 10 kpsi), the extra volume expansion was less than 2 cc, which was about 3-4% of the initial volume of loop flow line 210 (i.e., 56 cc).

Additionally, a correction term for temperature-dependent expansion may be added to the volume model of equation (3). The Young's modulus of regular steel only decreases about 3-4% from room temperature to 200° C. The temperature effect on the expansion of elastomeric seals, however, is large, but their total exposed area to fluid is relatively small in comparison with the metal area of flow line 210 and PVCU 212. Therefore, it seems likely that the volume model of equations (3) and (4) is only weakly dependent on temperature for many applications. In order words, the calibration results obtained at 80° C. previously should be applicable to the fluid at other temperatures. To determine this, results of the first test were compared the results from a second test. This second test was similar to the first test, except it was conducted at a temperature of 145° C.

Figure 8:
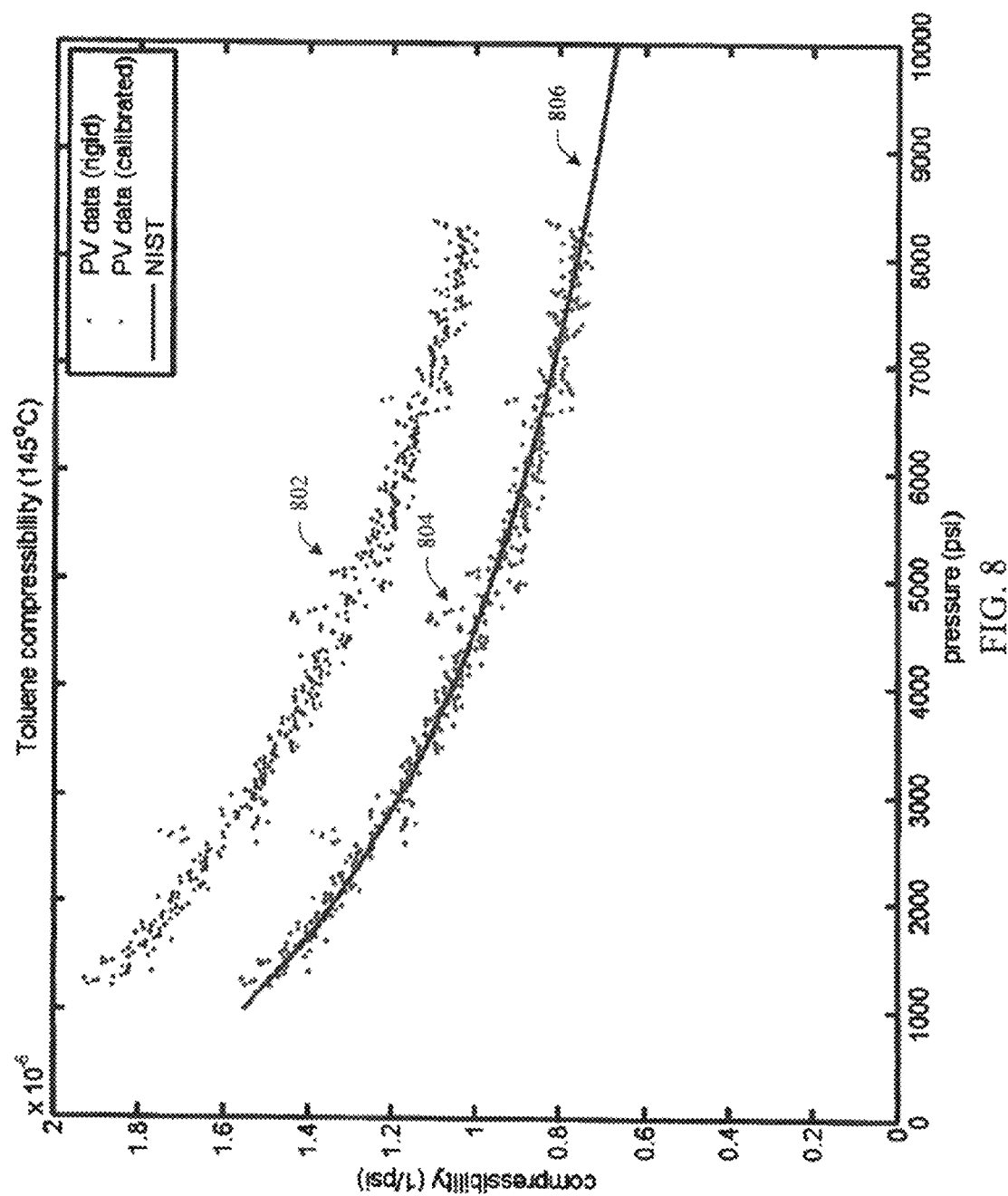
FIG. 8 shows the comparison of computed and reference compressibility profiles of toluene at 145° C.

FIG. 8 shows the comparison of computed and reference compressibility profiles of toluene at 145° C. As stated, this data was obtained using similar equipment and procedures to the first test, aside from the difference in temperature. The green dots 802 were obtained with the rigid volume model (equation (2)) and the red dots 804 were obtained with the calibrated model (equation (4)), respectively. To check whether the calibration results of the first test (at 80° C.) were accurate at 145° C., the calibration results of the first test (i.e., $\alpha=0.24$ cc/kpsi and $\beta=-6.0$ e$-3$ cc/kpsi$^2$) were used in the calibrated model to obtain the results shown at 804. Blue curve 806 is the reference compressibility profile at 145° C. from NIST REFPROP. As is apparent from FIG. 8, there was a very good agreement between the computed compressibility profile using the calibrated volume model and NIST reference compressibility profile. This example also demonstrates the insensitivity of the volume model with respect to temperature.

Figure 9:
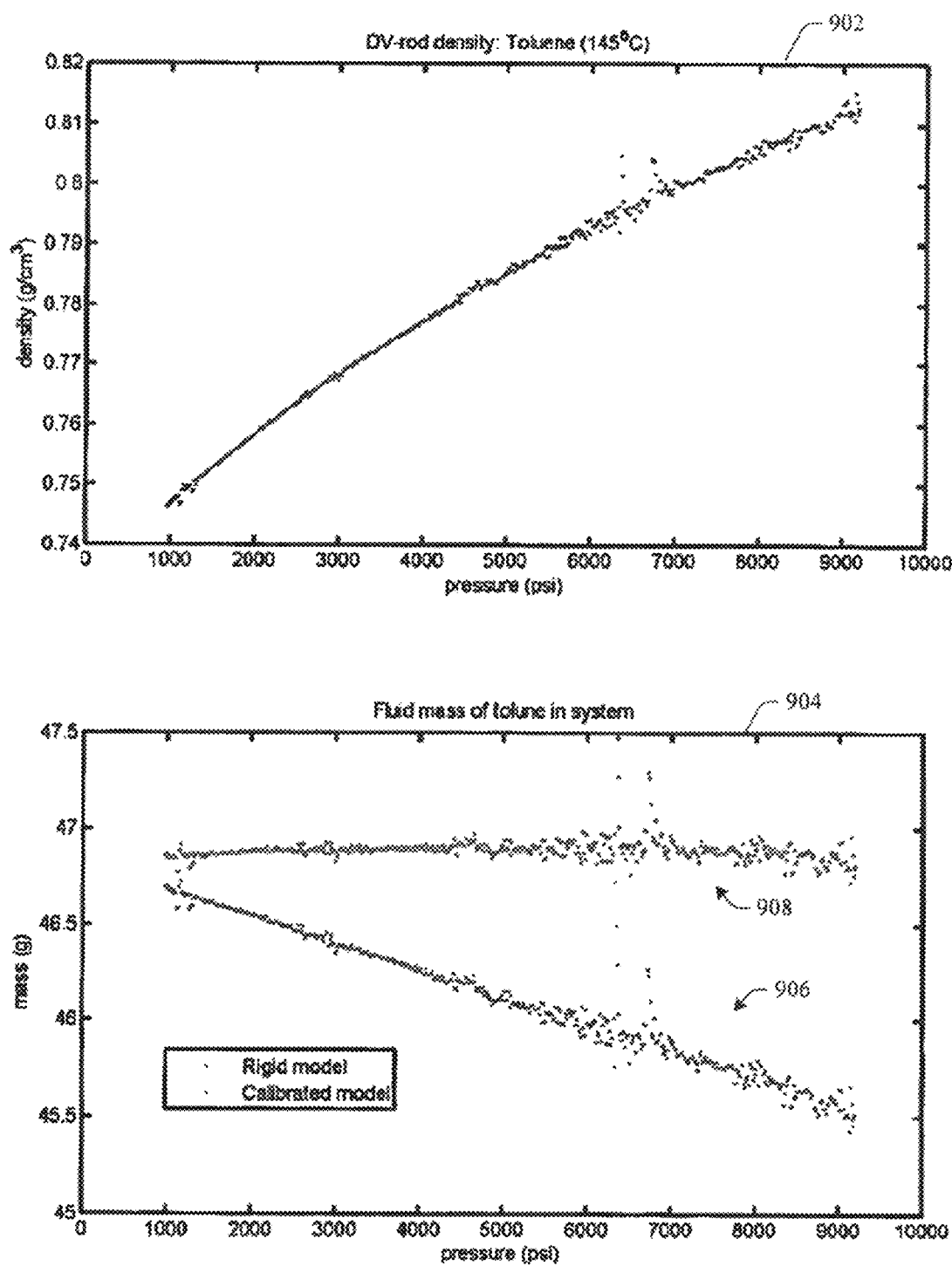
FIG. 9 shows density and mass plots of toluene at 145° C. that can be used for cross validation or consistency check of a system calibration.

Additionally, the second test also used density data from DV-rod 218 to validate the calibrated model. FIG. 9 shows the density of toluene as computed by DV-rod 218 at 145° C. in plot 902 and the computed mass in the system during depressurization in plot 904. With the rigid volume model, the computed mass (i.e., green dots) 906 showed a systematic decreasing trend with increasing pressure, whereas the computed mass 908 with the calibrated model red dots) was nearly a constant over the entire pressure range. Once again, the consistency of these results with the conservation of mass in a closed system validated the calibrated model used to derive the fluid mass in the system, as shown at 908.

Data from a third test showed that the calibration results were consistent with a different known fluid, indicating that the results are not sensitive to choice of reference fluid. In the third test, loop flow line 210 was initially filled with heptane, which was subsequently displaced by gas condensate. As with the first test, the third test was conducted at the temperature of 80° C. and the maximum pressure of 10 kpsi. As with toluene, the known (or reference) heptane compressibility (as a function of pressure) at 80° C. was obtained from NIST REFPROP (Reference Fluid Thermodynamic and Transport Properties Database).

Figure 10:
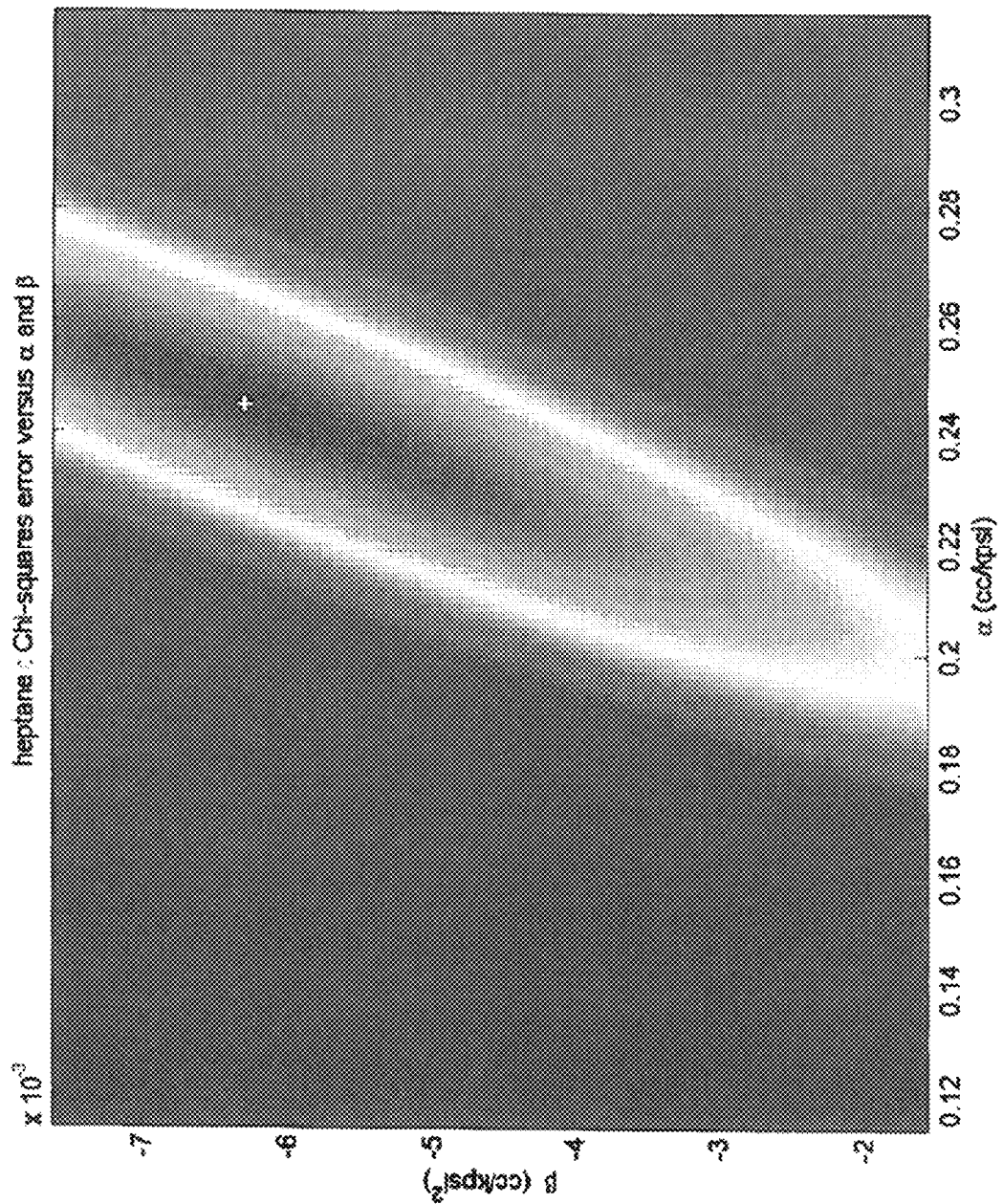
FIG. 10 shows a 2D display of computed chi-square errors between reference and test data related to heptane compressibility at 80° C.

Continuing the discussion of the figures, FIG. 10 shows the 2D display of computed chi-square errors based on the recorded heptanes data. The minimum of chi-square errors occurred at about $\alpha=0.243$ cc/kpsi and $\beta=-6.4$ e$-3$ cc/kpsi$^2$, which was very close to the previous toluene calibration results (i.e., $\alpha=0.24$ cc/kpsi and $\beta=-6.0$ e$-3$ cc/kpsi). In fact, these two sets of $\alpha$ and $\beta$ produced nearly identical chi-square errors, confirming the insensitivity of the calibration techniques discussed herein to choice of reference fluid 104. For consistency and ease of comparison, the rest of the results presented herein will use the same calibration parameters (i.e., $\alpha=0.24$ cc/kpsi and $\beta=-6.0$ e$-3$ cc/kpsi$^2$) as before for the calibrated model of equation (4).

Figure 11:
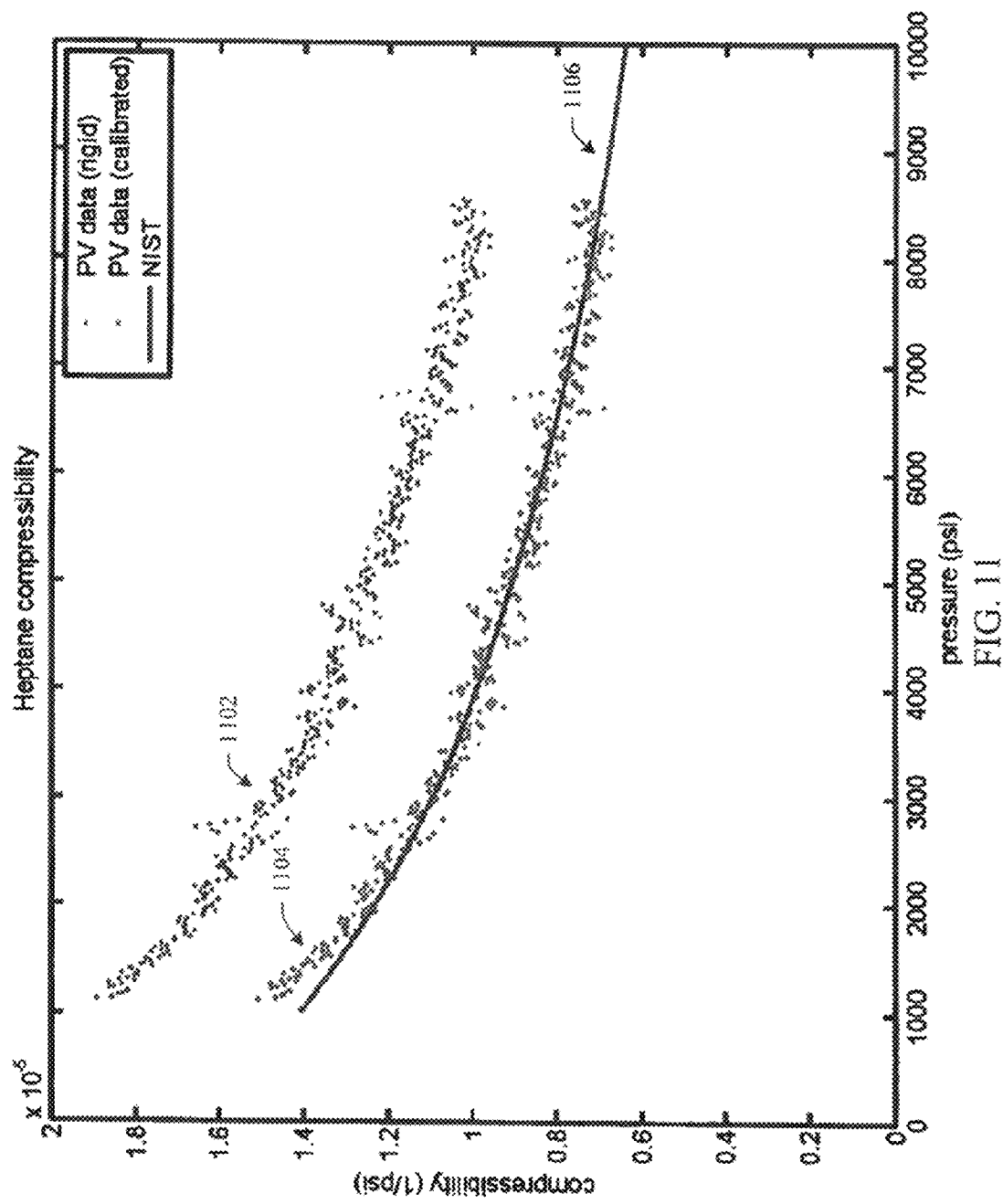
FIG. 11 shows the comparison of computed and reference heptane compressibility profiles at SOC.

Turning to FIG. 11, a graph is shown indicating the comparison of computed and reference heptane compressibility profiles. The green dots represent the computed compressibility profile 1102 obtained with the rigid volume model, whereas the red dots are the compressibility profile 1104 obtained with the calibrated model. Blue curve 1106 is the reference compressibility profile from NIST REFPROP. Similar to the previous observations, the fluid compressibility based on the rigid model was significantly off from the reference, whereas the fluid compressibility based on calibrated model was in a very good agreement with the reference, except some mismatch below 2000 psi. If necessary, the agreement between the calibrated model and the reference can be improved by using a different approximation than that of equation (4), such as a higher order polynomial, etc.

Figure 12:
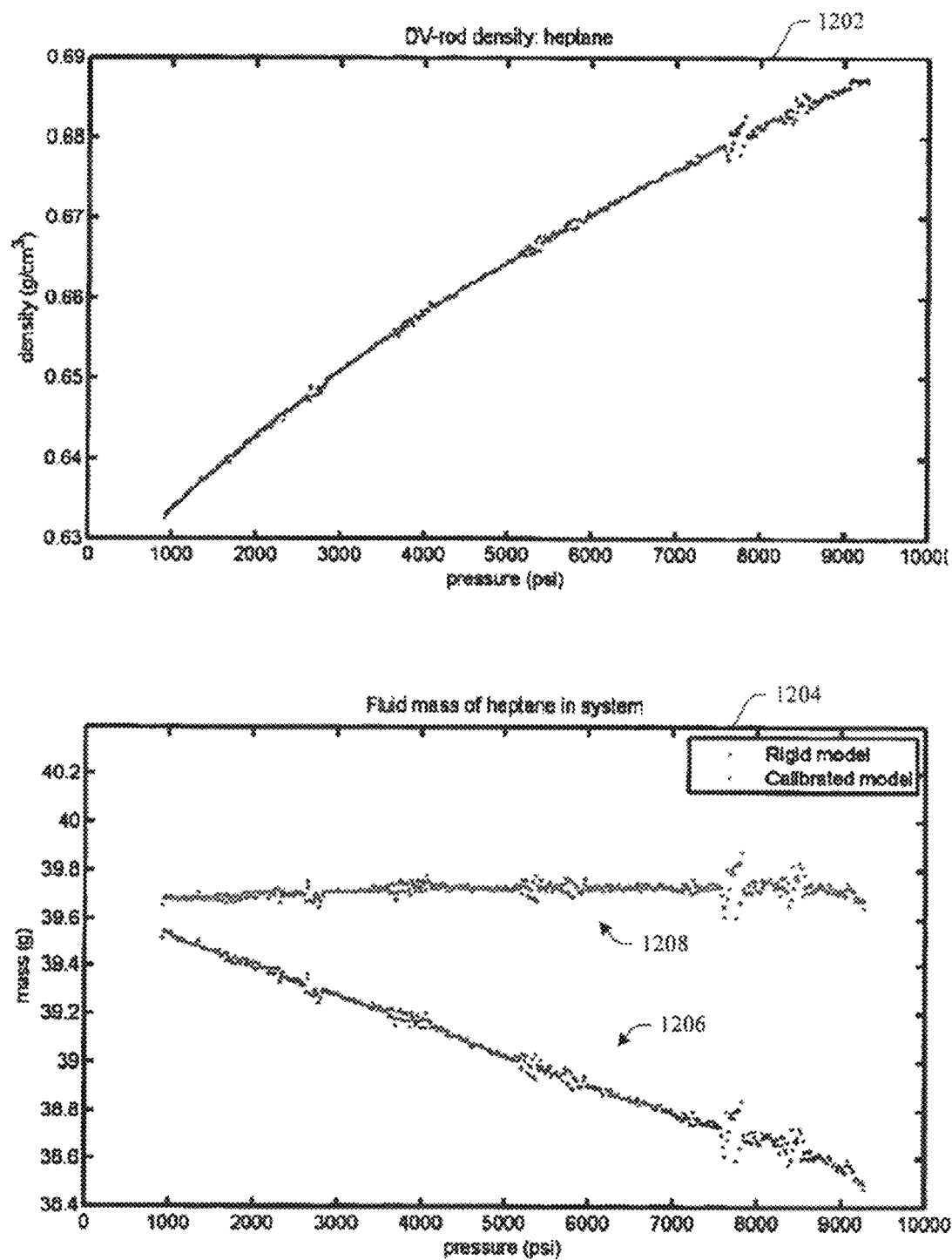
FIG. 12 shows density and mass plots of heptane at 80° C. that can be used for cross validation or consistency check of a system calibration.

FIG. 12 shows the validation of calibrated model using the density of heptane as acquired during depressurization by DV-rod 218. The density data is shown in plot 1202, while the mass as calculated from the density data and volume model is shown in plot 1204. With the rigid volume model, the computed mass green dots) 1206 showed a systematic decreasing trend with increasing pressure, whereas the computed mass 1208 with the calibrated model of equation (4) (i.e., red dots) was nearly a constant over the entire pressure range.

Figure 13:
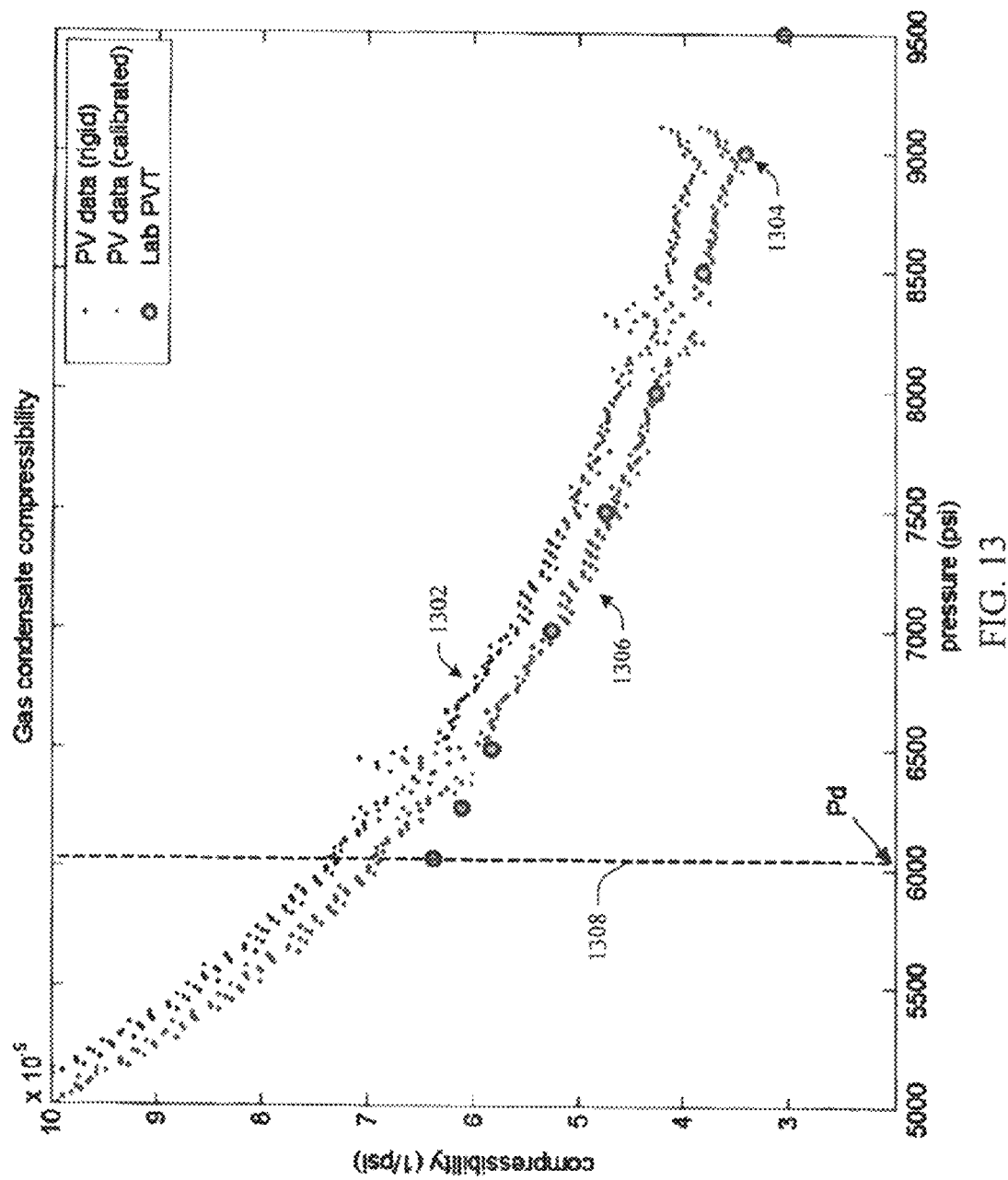
FIG. 13 shows a comparison of computed and laboratory compressibility profiles of gas condensate.

In the third test, as noted before, the heptane in the system was replaced by gas condensate. Using the PV data acquired from the depressurization of gas condensate, compressibility of gas condensate was computed. FIG. 13 shows the comparison of computed and PVT compressibility profiles of gas condensate. The green dots show the compressibility 1302 using the rigid model, which does not show good agreement with the PVT lab compressibility profile 1304, when compared with the compressibility profile 1306, using the calibrated model of equation (4), as shown by the red dots. It is notable that the calibrated model works quite well for high compressibility fluid such as gas condensate. The success of the model is demonstrated by the good agreement between the computed compressibility 1306 using the calibrated model (i.e., red dots) and the PVT compressibility blue circles) profile 1304. The dew point pressure of gas condensate is indicated by dashed line 1308.

Figure 14:
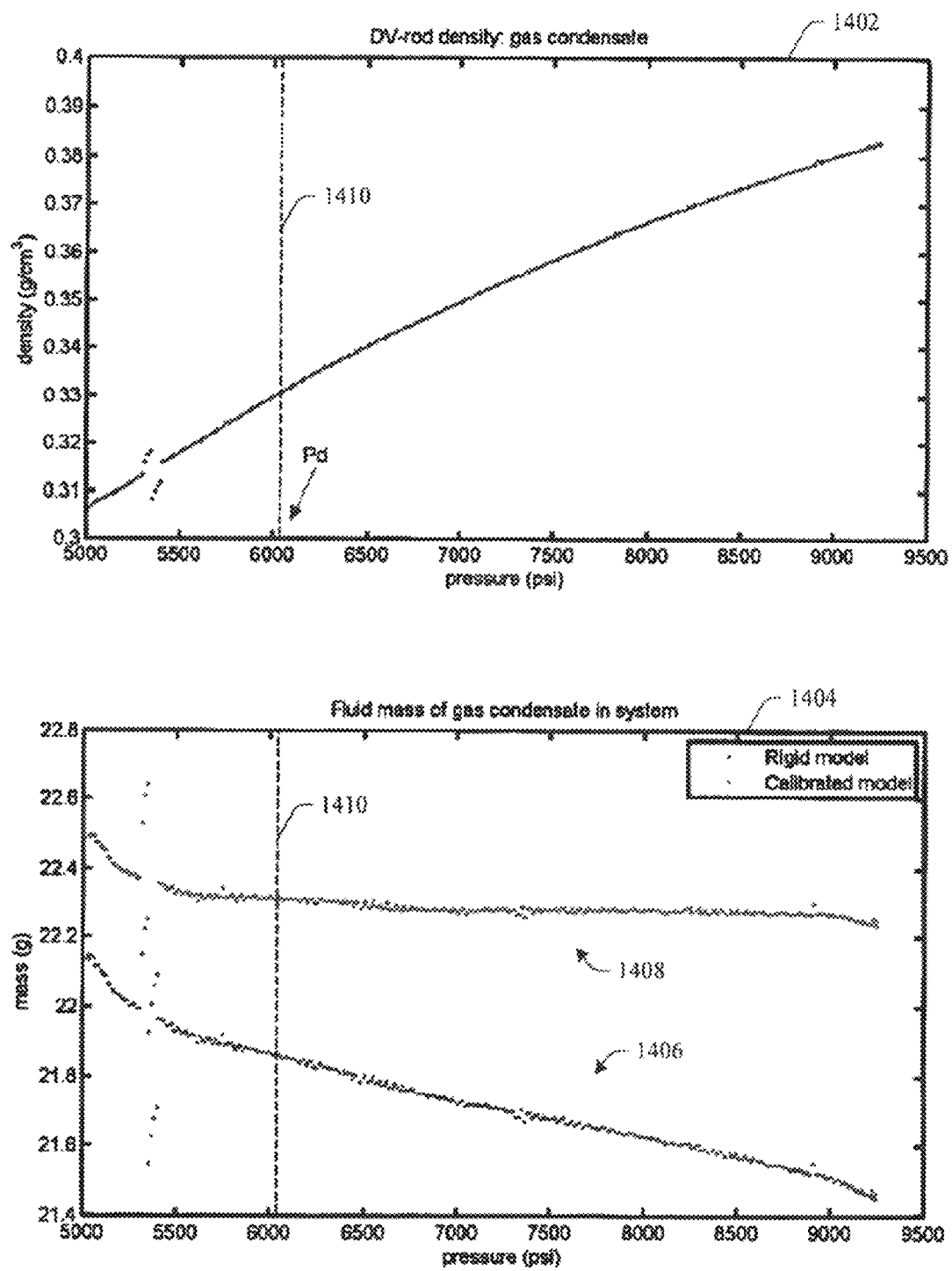
FIG. 14 shows density and mass plots of gas condensate that can be used for cross validation or consistency check of a system calibration.

Similar to FIGS. 5 and 9, FIG. 14 shows the validity of the calibrated model using the density acquired by DV-rod 218 during depressurization of gas condensate. Plot 1402 shows the density of gas condensate as calculated by DV-rod 21S, while plot 1404 shows the computed mass based on the rigid volume model at 1406 and based on the calibrated volume model at 1408. The dew point pressure of gas condensate is indicated by dashed line 1410.

Although the specific experimental results presented focused on specific sensor results, the calibration systems, methods, and techniques described herein are applicable to other sensors in the system and can be beneficial when used in conjunction with more than just those aspects discussed in the experiments. For example, a fluid sensor designed to measure certain properties of fluids often requires some calibration parameters to be determined. With a known fluid (therefore, known fluid properties) captured in the system, one can tune and adjust the calibration parameters so that the calibrated sensor is capable of measuring the known fluid properties. A vibrating wire sensor, designed to measure the fluid viscosity, is one specific example. In such an example, the physical properties of the wire (such as internal damping, radius, etc.)

are calibration parameters that can be determined with the known calibration fluid in the system. The calibration techniques, methods, etc., discussed herein can be applied to other sensors, as well, based on properties of those sensors. Additionally, aspects of the subject innovation can include cross-validating the multi-sensor measurements as described herein (e.g., in connection with conservation of mass, etc.), or in other methods. This cross-validation can be used to detect potential anomalies that may have occurred in the system.

Additionally, it is possible to use a different model than the one of equations (3) and (4), such as one based at least in part on the properties of the materials of the system, including temperature variations, etc. Even though the effect of these additional corrections would be small, the small mismatch (e.g., as is more apparent at low pressures in FIG. 11) may be reduced with more correction terms included, including one or more with dependence based at least in part on the properties of the materials of the system, including temperature variations, etc.

In view of the aspects and features described, methodologies that may be implemented in accordance with embodiments of the subject innovation will be better appreciated with reference to the figures. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated, acts may be required to implement a methodology in accordance with the innovation.

Figure 15:
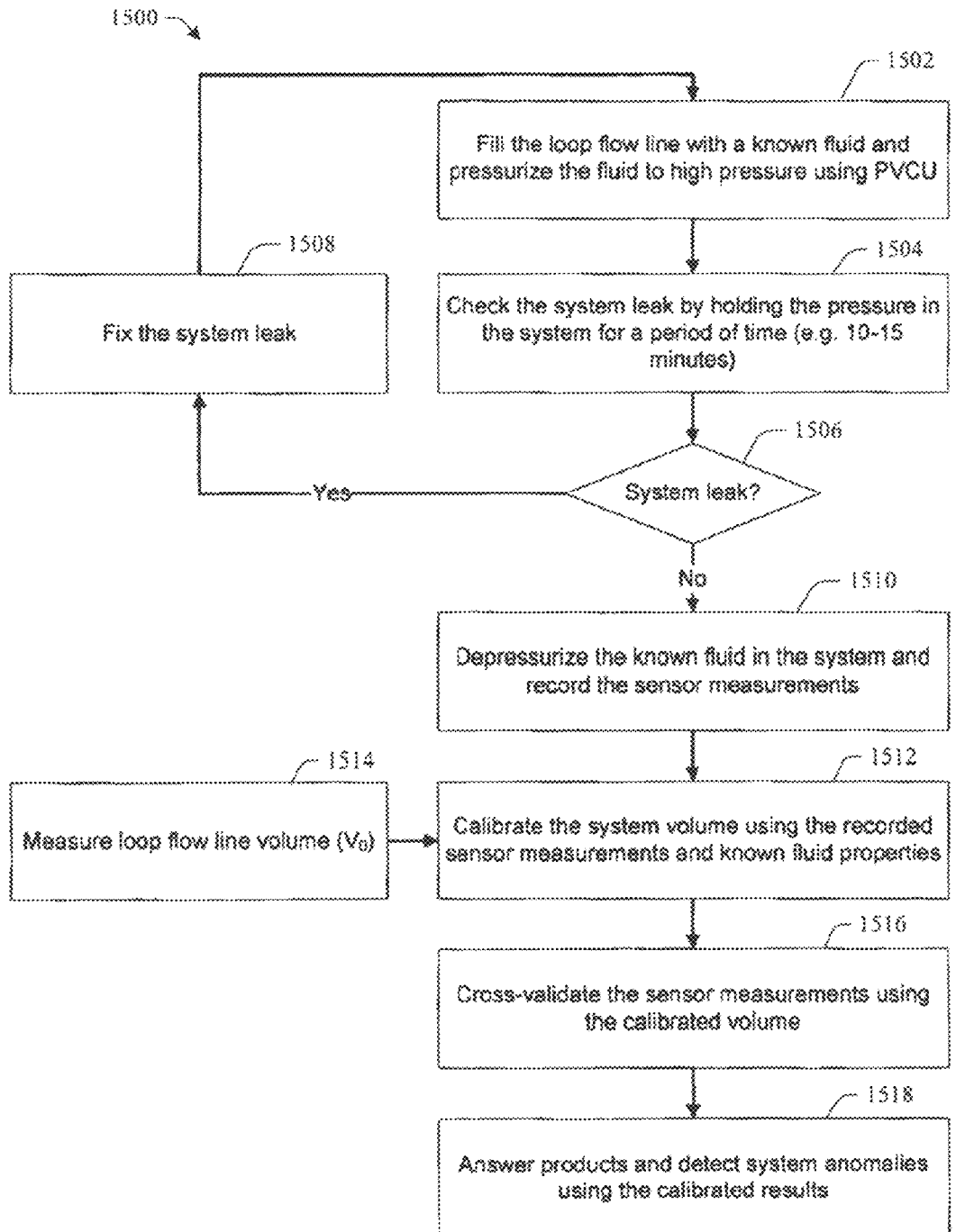
FIG. 15 shows a flowchart of at least a portion of a method of calibrating a system in accordance with aspects of the subject innovation.

Returning to the discussion of the figures, FIG. 15 shows a flowchart of a method 1500 of calibrating a system in accordance with aspects of the subject innovation. Method 1500 can begin at step 1502, where a variable volume container or loop flow line can be filled with a known fluid. The variable volume container or loop flow line can then be contracted (e.g., the fluid may be pressurized) to a high pressure, for example, via a PVCU such as PVCU 106 (or PVCU 212). At step 1504, the system can be checked for leaks, for example by maintaining the pressure or volume in the system at an approximately constant value for a period of time (e.g., about 10-15 minutes or more, etc.). At step 1506, the system can be checked for a leak, which can be determined through one of a number of ways, for example, if there is a trend of pressure change during the period of time when the pressure is not actively changed, during step 1504. If a leak has been found at step 1506, the method can continue at step 1508, where the system leak can be fixed and the method can begin again at step 1502. Alternatively or additionally, steps 1502 through 1510 can be conducted by varying a different independent variable, for example, temperature, etc., in place of pressure.

If no leak has been detected at step 1506, the method can continue at step 1510, where the variable volume container or loop flow line can be expanded (e.g., the known or reference fluid can be depressurized) and sensor measurements can be recorded. At step 1512, the system volume can be calibrated based at least in part on the recorded sensor measurements, properties of the known or reference fluid (e.g., from NIST REFPROP, based on independent measurements such as in a PVT laboratory, etc.). This calibration can also depend on the volume of the loop flow line or variable volume container at some constant pressure, such as zero pressure or room pressure ($V_0$). The volume of the loop flow line or variable volume container at a constant pressure (e.g., $V_0$) can be determined separately (e.g., as shown below in FIG. 16, etc.) and incorporated into the calibration, as shown at step 1514. The calibration can be based on any of the calibration techniques described herein, including those of equations (3) or (4), variations thereof as described herein or as would be apparent to a person of ordinary skill in the art in light of the present disclosure. etc. in some aspects, a determination can be made whether the measurements of the system as determined based on one or more calibrated system parameters correspond to properties of the known or reference fluid within a threshold (e.g., wherein the determination of whether it is with the threshold can be based on regression analysis, the calculation of an error such as chi-square error, etc.), and if not, a revised calibration of greater accuracy can be used.

Optionally, at step 1516, the sensor measurements can be cross-validated using the calibrated volume. For example, this can include calculating a mass based on density data obtained by one or more sensors and determining whether and to what extent the mass remains constant (e.g., as determined by regression analysis, etc.).

At step 1518, the calibrated system can be implemented by performing one or more test procedures on at least one fluid sample. In step 1518, answer products can be determined used at least in part on recorded sensor measurements of the at least one fluid sample and the calibrated system volume. Additionally, system anomalies can be detected, e.g., based on a determination that fluid properties (e.g., total fluid mass) determined based on one or more calibrated system parameters deviate from expected values. The calibration techniques and methods discussed herein can be used to calibrate a system at least one of initially, periodically, or intermittently. Alternatively or additionally, method 1500 can be conducted by varying a different independent variable, for example, temperature, etc., in place of pressure, and performing measurements, calibration, etc., on the basis of that independent variable (e.g., based on thermal expansion instead of compressibility, and with volume or some other system parameter as a function of temperature, etc.).

Figure 16:
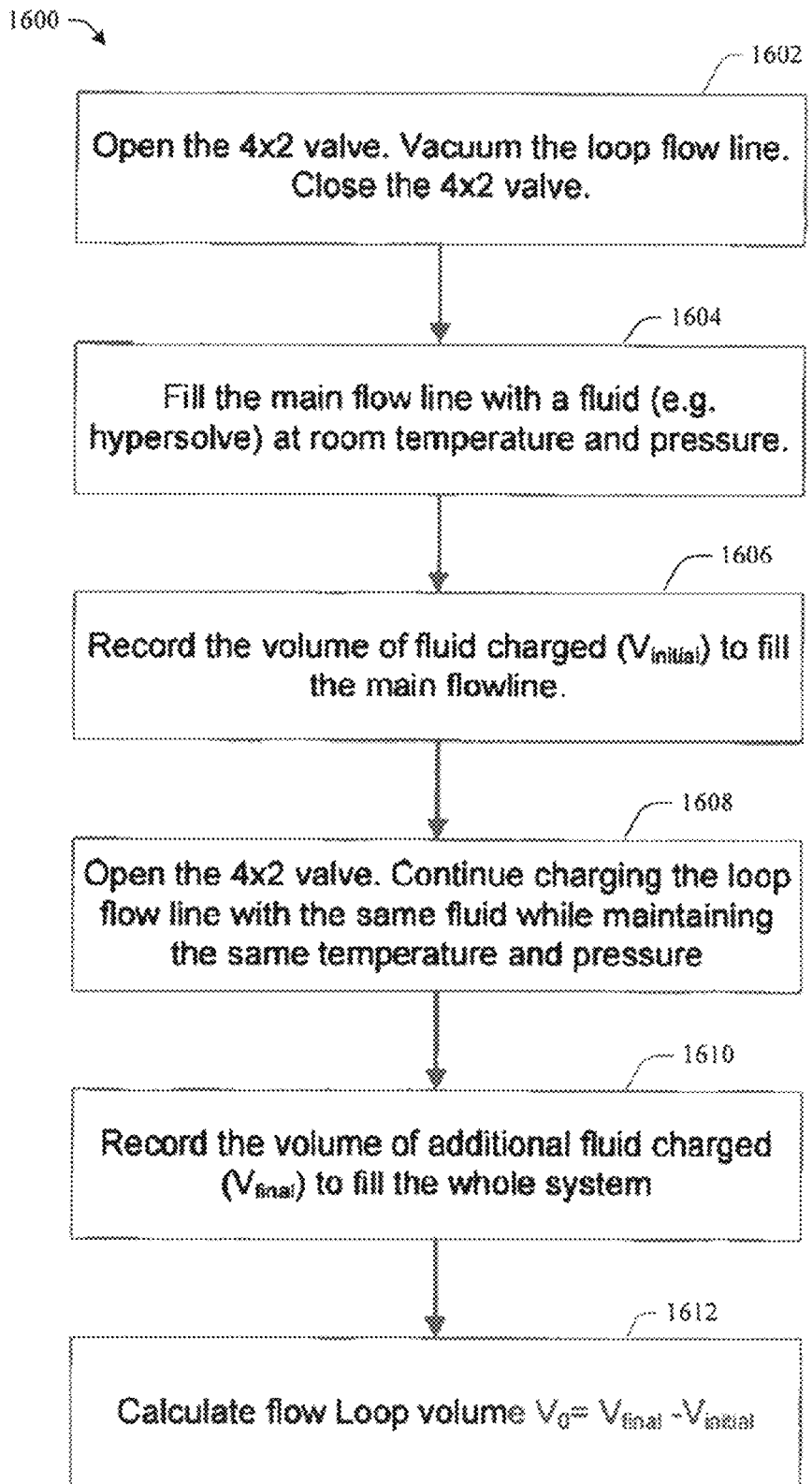
FIG. 16 illustrated a method for calculating the volume of a loop flow line of a variable volume container in accordance with aspects of the subject innovation.

Turning to FIG. 16, illustrated is a method 1600 for calculating the volume of a loop flow line or variable volume container in accordance with aspects of the subject innovation. At step 1602, the loop flow line or variable volume container can be cleared. For example, for a system connected to a main flow line via a 4-by-2 valve, this can include opening the 4-by-2 valve, vacuuming the loop flow line, and closing the 4-by-2 valve. Turning to step 1604, the main flow line or variable volume container can be filled with a fluid (e.g., hypersolve, etc.) at room temperature and pressure. At step 1606, a volume of fluid required or charged to fill a main flow line or similar container ($V_{initial}$) connected to the loop flow line or variable volume container can be recorded. In many applications, this fluid can be at a noticeably higher pressure than that of the fluid in the loop flow line or variable volume container. Next, at step 1608, a 4-by-2 valve or other connection to a main flow line or similar container can be opened, and the loop flow line or variable volume container can be filled with the fluid in the main flow line or similar container by continuing charging or filling the loop flow line or variable volume container with the same fluid as the main flow line or similar container, while maintaining the same temperature and pressure. Then at step 1610, the volume of additional fluid charged or required to ($V_{final}$) fill the whole system (e.g., the main flow line or similar container and the loop flow line or variable volume container) can be recorded. The method can conclude at step 1612, where the volume of the loop flow line or variable volume container can be calculated as the difference between the volumes recorded at steps 1610 and 1606: $V_0 = V_{final} - V_{initial}$.

Figure 17:
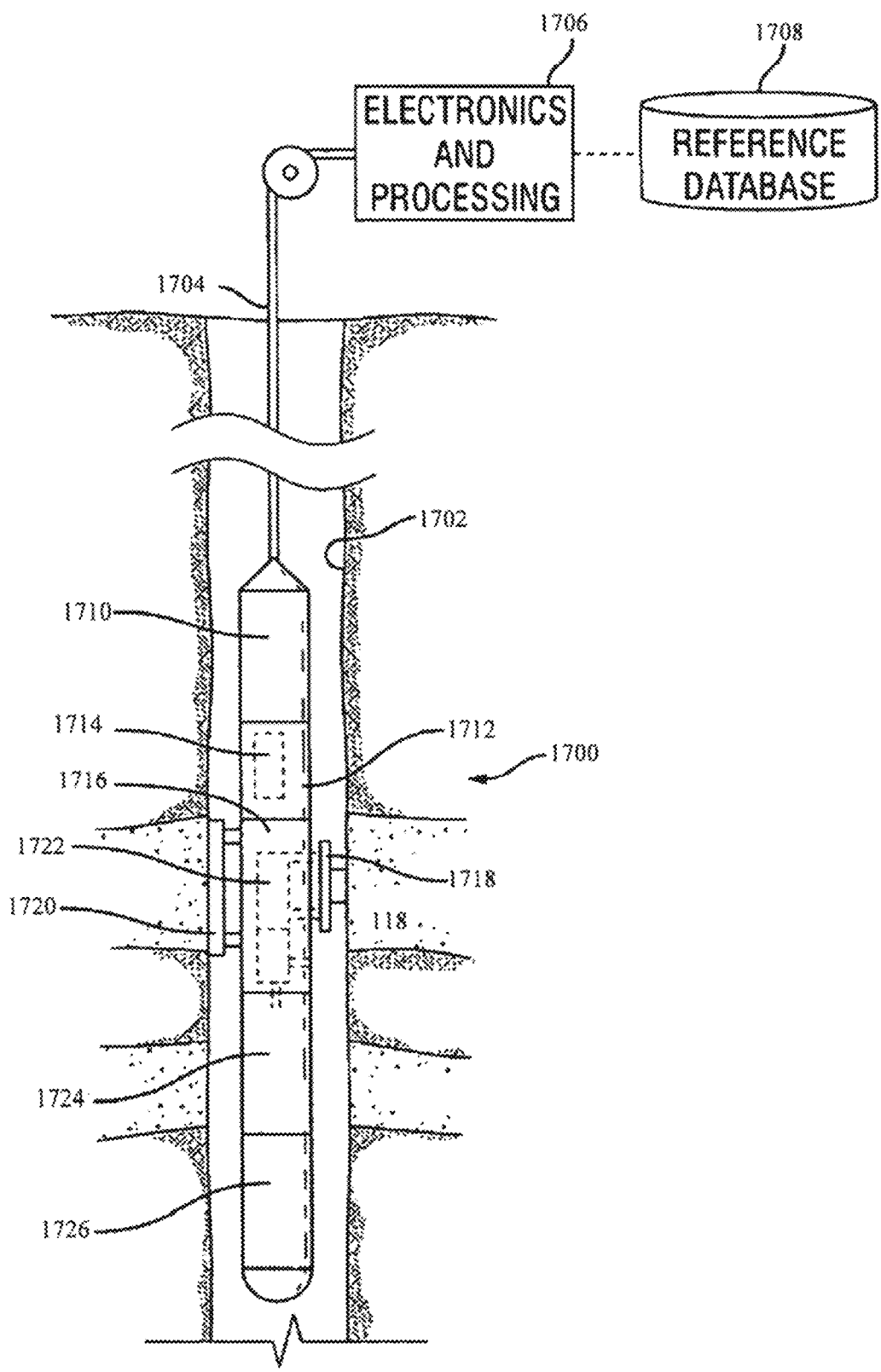
FIG. 17 illustrates an example wireline tool that may be used in connection with systems and methods of the subject innovation.

FIG. 17 depicts an example wireline tool 1700 that may be used to extract and analyze formation fluid samples in accordance with the example methods and apparatus described herein. As shown in FIG. 17, the example wireline tool 1700 can be suspended in a borehole or wellbore 1702 from the lower end of a multiconductor cable 1704 that can be spooled on a winch (not shown) at the surface. At the surface, the cable 1704 can be communicatively coupled to an electronics and processing system 1706. The electronics and processing system 1706 may include or be communicatively coupled to a reference database 1708 that may be used to store reference measurement values of reference fluids that can be used in calibrating systems and methods in aspects of the subject innovation. The wireline tool 1700 can include an elongated body 1710 that can include a collar 1712 having a downhole control system 1714 configured to control extraction of formation fluid from a formation 118, perform measurements on the extracted fluid, and to control systems or implement methods described herein to determine measurements on fluids based at least in part on calibrated system parameters.

The example wireline tool 1700 can also include a formation tester 1716 having a selectively extendable fluid admitting assembly 1718 and a selectively extendable tool anchoring member 1720 that can be respectively arranged on opposite sides of the elongated body 1710. The fluid admitting assembly 1718 can be configured to selectively seal off or isolate selected, portions of the wall of the wellbore 1702 to fluidly couple to the adjacent formation 118 and draw fluid samples from the formation 118. The formation tester 1716 can also include a fluid analysis module 1722 through which the obtained fluid samples can flow. The sample fluid may thereafter be expelled through a port (not shown) or it may be sent to one or more fluid collecting chambers 1724 and 1726 which may receive and retain the formation fluid samples for subsequent testing at the surface or a testing facility.

In the illustrated example, the electronics and processing system 1706 and/or the downhole control system 1714 are configured to control the fluid admitting assembly 1718 to extract fluid samples from the formation 118 and to control the fluid analysis module 1722 to measure the fluid samples. In some example implementations, the fluid analysis module 1722 may be configured to analyze the measurement data of the fluid samples as described herein, such as based at least in part on one or more calibrated system parameters. In other example implementations, the fluid analysis module 1722 may be configured to generate and store the measurement data and subsequently communicate the measurement data to the surface for analysis at the surface. Although the downhole control system 1714 is shown as being implemented separate from the formation tester 1716, in some example implementations, the downhole control system 1714 may be implemented in the formation tester 1716.

As described in greater detail below, the example wireline tool 1700 may be used in conjunction with the example methods and apparatus described herein to obtain measurements related to phase behavior and fluid properties based at least in part on one Of more calibrated system parameters. For example, the formation tester 1716 may include one or more sensors, fluid analyzers and/or fluid measurement units disposed adjacent a flow line and may be controlled by one or both of the downhole control system 1714 and the electronics and processing system 1706 to determine the phase behavior, fluid properties, or other characteristics of fluid samples extracted from, for example, the formation 118. More specifically, the example wireline tool 1700 can be configured to extract fluid samples from the formation 118 and to determine phase behavior or fluid properties of the fluid samples, based at least in part on calibrated values of one or more system parameters. Further, the example wireline tool 1700 can be configured to perform in situ calibration of systems and methods as described herein by determining calibrated values of one or more system parameters based at least in part on measurements conducted on a reference fluid.

Figure 20:
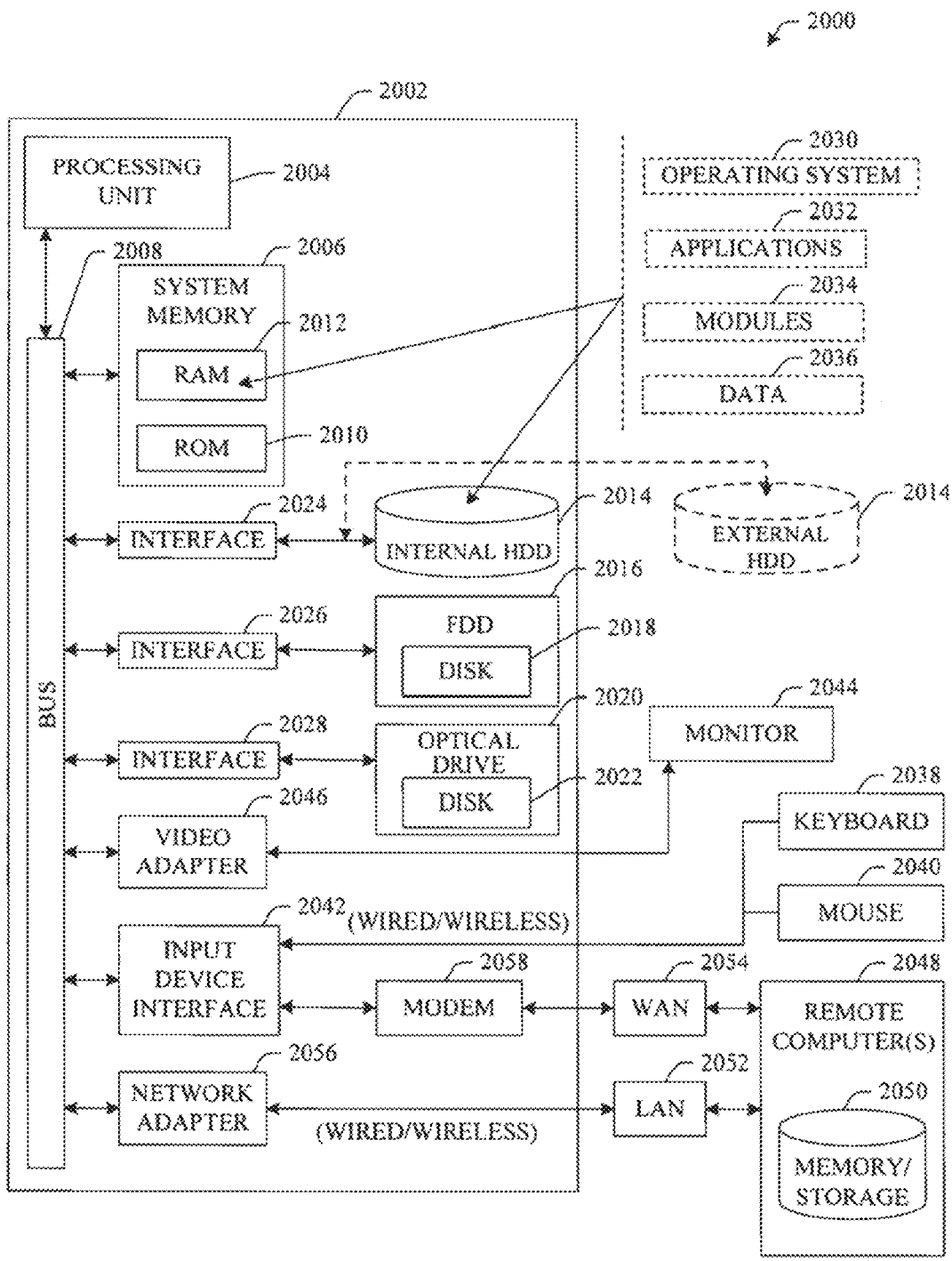
FIG. 20 illustrates a block diagram of a computer operable to execute in conjunction with aspects of the disclosed architecture.

The data processing associated with the example methods described herein may be performed by a processing unit or computer (e.g., as shown in FIG. 20) in the formation tester 1716 and/or within the fluid analysis module 1722, the downhole control system 1714, the electronics and processing system 1706, and/or within any other processing unit local or remote relative to the wireline tool 1700.

Figure 18:
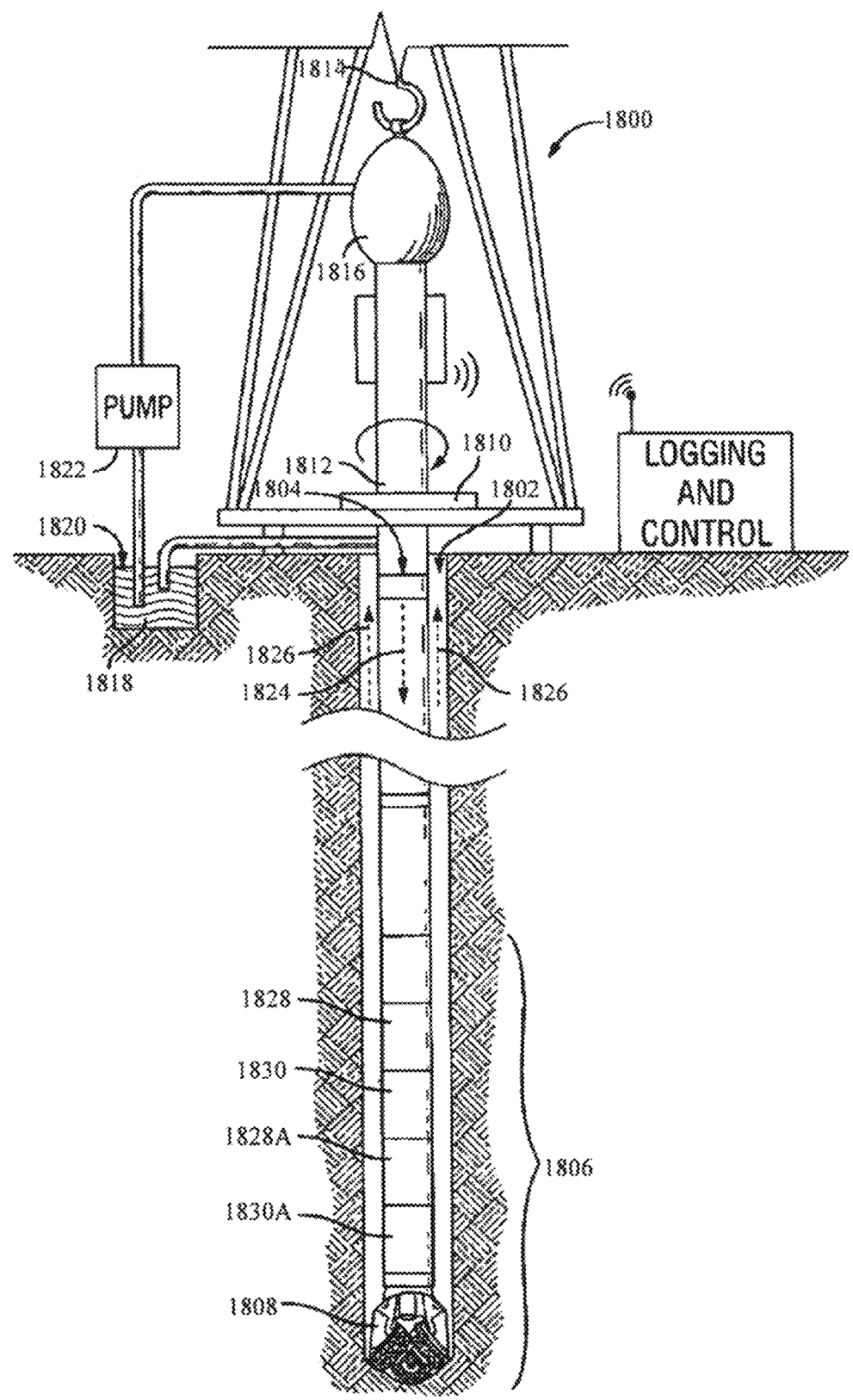
FIG. 18 illustrates an example while-drilling tool that may be used in connection with systems and methods of the subject innovation.

FIG. 18 illustrates a wellsite system in which one or more aspects of the subject disclosure may be employed. The wellsite and associated assembly 1800 can be onshore or offshore. In the example system of FIG. 18, a borehole 1802 is formed in subsurface formations by rotary drilling in a manner that would be well understood by a person of skill in the art in light of the subject disclosure. Embodiments of the subject disclosure can also use directional drilling.

A drill string 1804 can be suspended within the borehole 1802 and can have a bottom hole assembly 1806 which can include a drill bit 1808 at its lower end. The surface system can include platform and derrick assembly 1800 positioned over the borehole 1802, and assembly 1800 can include a rotary table 1810, kelly 1812, hook 1814 and rotary swivel 1816. The drill string 1804 can be rotated by the rotary table 1810, energized by means not shown, which can engage the kelly 1812 at the upper end of the drill string. The drill string 1804 can be suspended from a hook 1814, attached to a traveling block (also not shown), through the kelly 1812 and a rotary swivel 1816 which permits rotation of the drill string relative to the hook. As is well known, a top drive system could alternatively be used.

In the example of this embodiment, the surface system can thither include drilling fluid or mud 1818 stored in a pit 1820 formed at the well site. A pump 1822 can deliver the drilling fluid 1818 to the interior of the drill string 1804 via a port in the swivel 1816, causing the drilling fluid to flow downwardly through the drill string 1804 as indicated by the directional arrow 1824. The drilling fluid can exit the drill string 1804 via ports in the drill bit 1808, and then can circulate upwardly through the annulus region between the outside of the drill string and the wall of the borehole, as indicated by the directional arrows 1826. In this manner, the drilling, fluid can lubricate the drill bit 1808 and can carry formation cuttings up to the surface as it is returned to the pit 1820 for recirculation.

The bottom hole assembly 1806 of the illustrated embodiment can comprise a logging-while-drilling (LWD) module 1828, a measuring-while-drilling (MWD) module 1830, a roto-steerable system and motor, and the drill bit 1808. The LWD module 1828 and/or the MWD module 1830 may be or comprise a tool that may be used to extract and analyze formation fluid samples in accordance with the example methods and systems described herein, such as that described in connection with FIG. 1 or 2. For example, the LWD module 1828 and/or the MWD module 1830 may include a system such as system 100 or the system of method 1500. The LWD module 1828 and/or the MWD module 1830 may further comprise a downhole control system and/or otherwise be configured to control extraction of formation fluid from a formation 118, perform measurements on the extracted fluid, and to control the systems or implement the methods described herein to calibrate one or more system parameters, to perform cross-validation, or both.

The LWD module 1828 can be housed in a special type of drill collar, as would be understood by a person of skill in the art in light of the subject disclosure, and can contain one or a plurality of known types of logging tools. It will also be understood that more than one LWD and/or MWD module can be employed, e.g. as represented at 1828A and 1830A. (References, to a module at the position of 1828 or 1830 can alternatively mean a module at the position of 1828A or 1830A, respectively, as well.) The LWD module includes capabilities for measuring, processing, and storing information, as well as for communicating with the surface equipment. In embodiments, one or more system parameters of the LWD module can be calibrated as described herein.

The MWD module 1830 can also housed in a special type of drill collar, as would be understood by a person of skill in the art in light of the subject disclosure, and can contain one or more devices for measuring characteristics of the drill string and drill bit. The MWD tool can further include an apparatus (not shown) for generating electrical power to the downhole system. This may typically include a mud turbine generator powered by the flow of the drilling fluid, it being understood that other power and/or battery systems may be employed. In aspects, the MWD module can include one or more of the following types of measuring devices: a weight-on-bit measuring device, a torque measuring device, a vibration measuring device, a shock measuring device, a stick slip measuring device, a direction measuring device, or an inclination measuring device.

Figure 19:
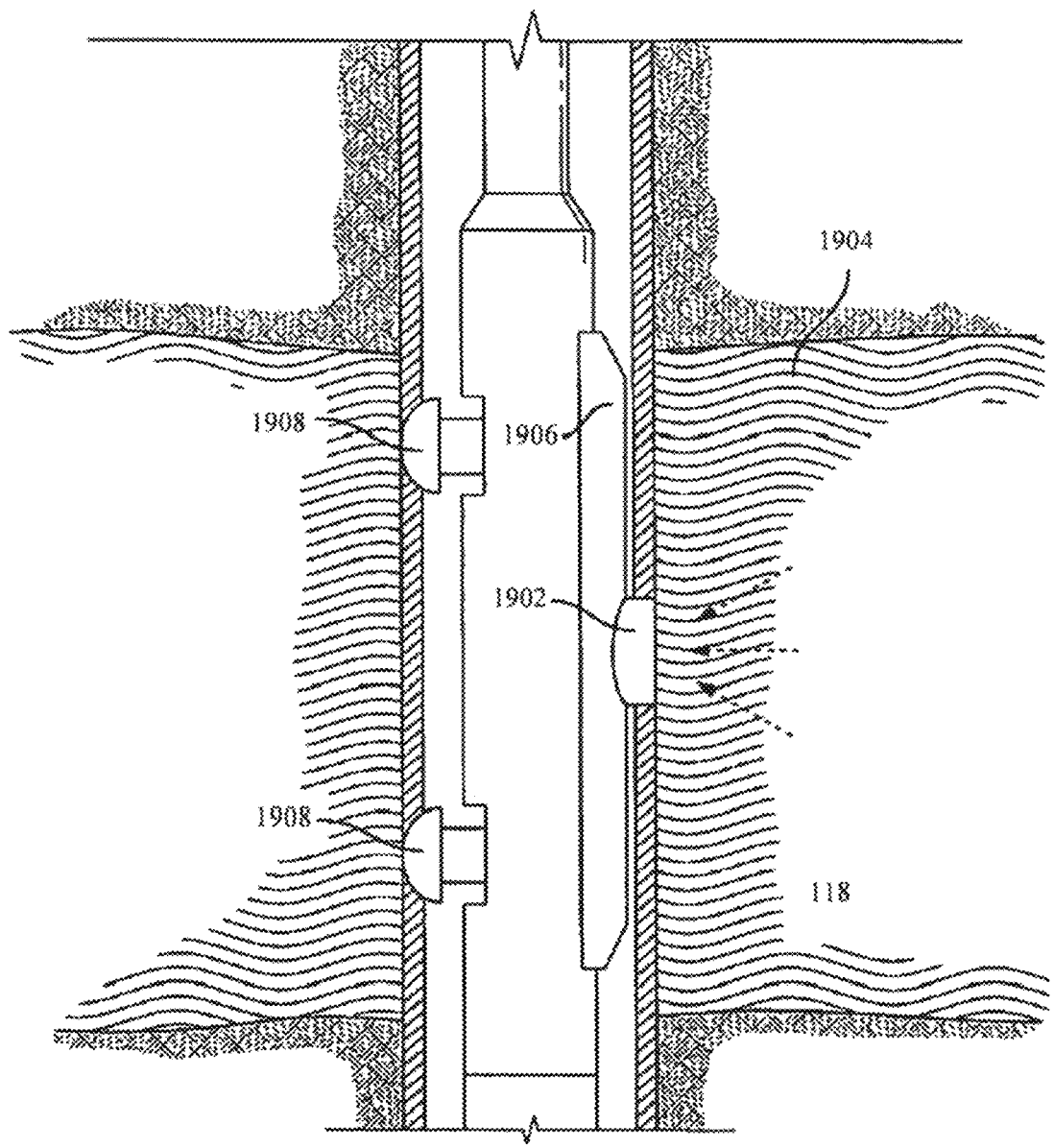
FIG. 19 illustrates a portion of the example while-drilling tool of FIG. 18.

FIG. 19 is a simplified diagram of a sampling-while-drilling logging device of a type described in U.S. Pat. No. 7,114,562, incorporated herein by reference, utilized as the LWD tool 1828 or part of an LWD tool suite 1828A. The LWD tool 1828 can be provided with a probe 1902 for establishing fluid communication with the formation and drawing the fluid 1904 into the tool, as indicated by the arrows. The probe may be positioned in a stabilizer blade 1906 of the LWD tool and extended therefrom to engage the borehole wall. The stabilizer blade 1906 can comprise one or more blades that are in contact with the borehole wall. Fluid drawn into the downhole tool using the probe 1818 may be measured to determine, for example, one or more of phase behavior or fluid properties. Additionally, the LWD tool 1828 may be provided with devices, such as sample chambers, for collecting fluid samples for retrieval at the surface. Backup pistons 1908 may also be provided to assist in applying force to push the drilling tool and/or probe against the borehole wall.

The example while-drilling tools shown in FIGS. 22 and 23 may be used in conjunction with the example methods and systems described herein to obtain measurements and answer products based at least in part on one or more calibrated system parameters. For example, the LWD module 1828 and/or the MWD module 1830 may include one or more sensors, fluid analyzers and/or fluid measurement units disposed adjacent a flow line and may be controlled by one or both of a downhole control system and a surface-located electronics and processing system to perform at least one of in situ calibration of one or more system parameters or take measurements based at least in part on one or more calibrated system parameters. Additionally, one or more sensors of the LWD module 1828 and/or the MWD module 1830 may be configured to perform cross-validation using one or more techniques described herein. One or more other aspects of the LWD module 1828 and/or the MWD module 1830 may be as described above with reference to the wireline tool 1700 shown in FIG. 17 and/or system 100.

Referring now to FIG. 20, there is illustrated a block diagram of a computer operable to execute in conjunction with aspects of the disclosed architecture. In order to provide additional context for various aspects of the subject innovation, FIG. 20 and the following discussion are intended to provide a brief, general description of a suitable computing environment 2000 in which various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network, in a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By was of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 20, the exemplary environment 2000 for implementing various aspects of the innovation includes a computer 2002, the computer 2002 including a processing unit 2004, a system memory 2006 and a system bus 2008. The system bus 2008 couples system components including, but not limited to, the system memory 2006 to the processing unit 2004. The processing unit 2004 can be any of various commercially available processors. Dual microprocessors and other multi-processor architectures may also be employed as the processing unit 2004.

The system bus 2008 can be any of several types of bus structure that may further interconnect to a memory bus (with or without a memory controller), a peripheral bus, and a local bus using any of a variety of commercially available bus architectures. The system memory 2006 includes read-only memory (ROM) 2010 and random access memory (RAM) 2012. A basic input/output system (BIOS) is stored in a non-volatile memory 2010 such as ROM, EPROM, EEPROM, which BIOS contains the basic routines that help to transfer information between elements within the computer 2002, such as during start-up. The RAM 2012 can also include a high-speed RAM such as static RAM for caching data.

The computer 2002 further includes an internal hard disk drive (HDD) 2014 (e.g., EIDE, SATA), which internal hard disk drive 2014 may also be configured for external use in a suitable chassis (not shown), a magnetic floppy disk drive (FDD) 2016. (e.g., to read from or write to a removable diskette 2018) and an optical disk drive 2020, (e.g., reading a CD-ROM disk 2022 or, to read from or write to other high capacity optical media such as the DVD). The hard disk drive 2014, magnetic, disk drive 2016 and optical disk drive 2020 can be connected to the system bus 2008 by a hard disk drive interface 2024, a magnetic disk drive interface 2026 and an optical drive interface 2028, respectively. The interface 2024 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 2002, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 2012, including an operating, system 2030, one or more application programs 2032, other program modules 2034 and program data 2036. All or portions of the operating system, applications, modules, and/or data can also be cached in the RAM 2012. It is appreciated that the innovation can be implemented with various commercially available operating systems or combinations of operating systems.

A user can enter commands and information into the computer 2002 through one or more wired/wireless input devices, e.g. a keyboard 2038 and a pointing device, such as a mouse 2040. Other input devices (not shown) may include a microphone, an IR remote control, a joystick, a game pad, a stylus pen, touch screen, or the like. These and other input devices are often connected to the processing unit 2004 through an input device interface 2042 that is coupled to the system bus 2008, but can be connected by other interfaces, such as a parallel port, an IEEE 1394 serial port, a game port, a USB port, an IR interface, etc.

A monitor 2044 or other type of display device is also connected to the system bus 2008 via an interface, such as a video adapter 2046. In addition to the monitor 2044, a computer typically includes other peripheral output devices not shown), such as speakers, printers, etc.

The computer 2002 may operate in a networked environment using logical connections via wired and/or wireless communications to one or more remote computers, such as a remote computer(s) 2048. The remote computer(s) 2048 can be a workstation, a server computer, a router, a personal computer, portable computer, microprocessor-based entertainment appliance, a peer device or other common network node, and typically includes many or all of the elements described relative to the computer 2002, although, for purposes of brevity, only a memory/storage device 2050 is illustrated. The logical connections depicted include wired/wireless connectivity to a local area network (LAN) 2052 and/or larger networks, e.g., a wide area network (WAN) 2054. Such LAN and WAN networking environments are commonplace in offices and companies, and facilitate enterprise-wide computer networks, such as intranets, all of which may connect to a global communications network, e.g., the Internet.

When used in a LAN networking environment, the computer 2002 is connected to the local network 2052 through a wired and/or wireless communication network interface or adapter 2056. The adapter 2056 may facilitate wired or wireless communication to the LAN 2052, which may also include a wireless access point disposed thereon for communicating with the wireless adapter 2056.

When used in a WAN networking environment, the computer 2002 can include a modem 2058, or is connected to a communications server on the WAN 2054, or has other means for establishing communications over the WAN 2054, such as by way of the Internet. The modem 2058, which can be internal or external and a wired or wireless device, is connected to the system bus 2008 via the serial port interface 2042. In a networked environment, program modules depicted relative to the computer 2002, or portions thereof, can be stored in the remote memory/storage device 2050. It will be appreciated that the network connections shown are exemplary and other means of establishing a communications link between the computers can be used.

The computer 2002 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi allows connection to the Internet from a couch at home, a bed in a hotel room, or a conference room at work, without wires. Wi-Fi is a wireless technology similar to that used in a cell phone that enables such devices, e.g., computers, to send and receive data indoors and out anywhere within the range of a base station. Wi-Fi networks use radio technologies called IEEE 802.1.1 (a, b, g, etc.) to provide secure, reliable, fast wireless connectivity, A Wi-Fi network can be used to connect computers to each other, to the Internet, and to wired networks (which use IEEE 802.3 or Ethernet). Wi-Fi networks operate in the unlicensed 2.4 and 5 GHz radio hands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fan within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
a variable volume container that alters at least one of a temperature and a pressure of a reference fluid;
a measurement component that records a first set of measurements of the reference fluid while the at least one of the temperature or the pressure of the reference fluid is altered;
an analysis component that determines a first answer product based at least in part on the first set of measurements and at least one system parameter, wherein the at least one system parameter is uncalibrated; and
a calibration component comprising instructions disposed on a non-transitory, machine readable medium, wherein the instructions are configured to monitor or control operations of the system to:
determine a calibration function based at least in part on a comparison between the first answer product and at least one known property of the reference fluid; and
calibrate the at least one system parameter based at least in part on the comparison, wherein the variable volume container additionally alters at least one of a temperature and a pressure of an unknown fluid sample, wherein the measurement component additionally records a second set of measurements of the unknown fluid sample while the at least one of the temperature and the pressure of the reference fluid is altered, and wherein the analysis component determines a second answer product based at least in part on the second set of measurements and the at least one system parameter as calibrated by the calibration component.

2. The system of claim 1, wherein the measurement component comprises at least two sensors, and the calibration component further cross-validates the calibration function based at least on one of the at least two sensors.

3. The system of claim 1, wherein the variable volume container maintains the reference fluid at an approximately constant pressure for a period of time, and wherein the measurement component determines whether there are leaks in the system based at least in part on measurements taken during the period of time.

4. The system of claim 1, wherein the calibration function is determined based at least in part on regression analysis.

5. The system of claim 1, wherein the system is implemented at least in part in a logging while drilling (LWD) tool.

6. The system of claim 1, wherein the system is implemented at least in part in a wireline tool.

7. A method, comprising:
filling a variable volume container of a system with a reference fluid;
altering, via the variable volume container, at least one of the temperature and the pressure of the reference fluid;
recording measurements, via one or more sensors, of the reference fluid while the at least one of the temperature and the pressure of the reference fluid is changing;
comparing, via a calibration component, the recorded measurements to at least one known property of the reference fluid;
calibrating, via the calibration component, at least one parameter of the system based at least in part on the comparison;
recording measurements, via the one or more sensors, of an unknown fluid sample; and
producing, via an analysis component, one or more answer products based at least in part on the recorded measurements of the unknown fluid sample and the one or more calibrated parameters of the system.

8. The method of claim 7, wherein the recorded measurements comprise pressure measurements.

9. The method of claim 8, further comprising determining a compressibility value based at least in part on the pressure measurements and the at least one parameter of the system.

10. The method of claim 8, wherein the calibrating the at least one parameter of the system comprises determining a calibrated value of at least one of the at least one parameter of the system such that the compressibility value as determined based on the calibrated value is substantially equal to a known value of the compressibility of the reference fluid.

11. The method of claim 7, further comprising:
checking the variable volume container for leaks while the reference fluid is at an increased pressure.

12. The method of claim 7, further comprising:
cross-validating the measurements by at least one of checking the system for anomalies and verifying that a total mass of the reference fluid remains about constant,
wherein the at least one sensor comprises at least two sensors, and the total mass is calculated based at least in part on measurements recorded by at least one of the at least two sensors.

13. The method of claim 7, wherein calibrating at least one parameter comprises calibrating a volume of the system as a function of pressure.

14. The method of claim 7, wherein calibrating the at least one parameter comprises approximating a portion of at least one of the parameters with a polynomial function.

15. The method of claim 7, wherein calibrating the at least one parameter comprises fitting the recorded measurements to the at least one property of the reference fluid via regression analysis.

16. The method of claim 15, further comprising:
re-calibrating at least one parameter of the system based at least in part on the comparison, wherein the re-calibrating occurs based on a determination that the recorded measurements are not within a threshold of the at least one known property of the reference fluid, and wherein the re-calibrating utilizes a more accurate calibration function than the calibrating.

17. The method of claim 7, wherein recording measurements, via the at least one sensor, of the unknown fluid sample is performed in a wireline tool.

18. The method of claim 7, wherein recording measurements, via the at least one sensor, of the unknown fluid sample is performed in a logging while drilling (LWD) tool.

* * * * *